US012721560B2

(12) United States Patent
Ren et al.

(10) Patent No.: US 12,721,560 B2
(45) Date of Patent: Sep. 1, 2026

(54) CIRCADIAN RHYTHM-BASED TRAINING DATA CORRECTION FOR DROWSINESS DETECTION SYSTEMS AND APPLICATIONS

(71) Applicant: NVIDIA Corporation, Santa Clara, CA (US)

(72) Inventors: Yuzhuo Ren, Sunnyvale, CA (US); Niranjan Avadhanam, Saratoga, CA (US); Varsha Hedau, Sunnyvale, CA (US); Zhengmin Zhang, Santa Clara, CA (US); Shelly Goel, Irving, TX (US)

(73) Assignee: NVIDIA Corporation, Santa Clara, CA (US)

( * ) Notice: Subject to any disclaimer, the term of this patent is extended or adjusted under 35 U.S.C. 154(b) by 150 days.

(21) Appl. No.: 18/407,924

(22) Filed: Jan. 9, 2024

(65) Prior Publication Data

US 2025/0221647 A1 Jul. 10, 2025

(51) Int. Cl.
*A61B 5/18* (2006.01)
*A61B 5/00* (2006.01)
(Continued)

(52) U.S. Cl.
CPC ................ *A61B 5/18* (2013.01); *A61B 5/162* (2013.01); *A61B 5/163* (2017.08); *A61B 5/372* (2021.01);
(Continued)

(58) Field of Classification Search
CPC ........... A61B 5/18; A61B 5/162; A61B 5/163; A61B 5/372; A61B 5/4857; A61B 5/6893;
(Continued)

(56) References Cited

U.S. PATENT DOCUMENTS

| | | | |
|---|---|---|---|
| 10,235,859 | B1 | 3/2019 | Hiles |
| 10,885,698 | B2 | 1/2021 | Muthler et al. |

(Continued)

FOREIGN PATENT DOCUMENTS

| | | | | |
|---|---|---|---|---|
| DE | 102015122245 A1 | 6/2017 | | |
| WO | 2017/102614 A1 | 6/2017 | | |
| WO | WO-2023218546 A1 * | 11/2023 | .......... | A61B 5/7267 |

OTHER PUBLICATIONS

Ghoddoosian et al., "A Realistic Dataset and Baseline Temporal Model for Early Drowsiness Detection", 2019 IEEE/CVF Conference on Computer Vision and Pattern Recognition Workshops (CVPRW), Long Beach, CA, USA, 2019, pp. 178-187 (Year: 2019).*

(Continued)

*Primary Examiner* — Vu Le
*Assistant Examiner* — Rachel Anne Ometz
(74) *Attorney, Agent, or Firm* — Shook, Hardy & Bacon L.L.P.

(57) ABSTRACT

In various examples, circadian rhythm-based data augmentation for drowsiness detection systems and applications are provided. Embodiments described herein may produce an estimated circadian rhythm for a test subject and/or vehicle driver or other machine operator or occupant, and use the pattern of that circadian rhythm to correct, confirm, calibrate, or otherwise augment drowsiness assessments derived from video image data. The position of a person in the context of their process C circadian cycle may be used as indication of their level of drowsiness. An estimated process C circadian cycle may be used to generate more accurate ground truth training data for training machine learning models, and may be used by real-time, in-vehicle drowsiness detection systems that infer driver drowsiness levels based on captured images. In various embodiments, a circadian rhythm drowsiness estimate may be used to correct, cali- (Continued)

brate, augment, and/or replace a drowsiness score predicted by a machine learning model.

20 Claims, 13 Drawing Sheets

(51) Int. Cl.
*A61B 5/16* (2006.01)
*A61B 5/372* (2021.01)
*B60W 60/00* (2020.01)
*G06V 10/774* (2022.01)
*G06V 20/59* (2022.01)

(52) U.S. Cl.
CPC .......... *A61B 5/4857* (2013.01); *A61B 5/6893* (2013.01); *A61B 5/7267* (2013.01); *B60W 60/00* (2020.02); *G06V 10/774* (2022.01); *G06V 20/597* (2022.01); *B60W 2540/229* (2020.02)

(58) Field of Classification Search
CPC ... A61B 5/7267; A61B 5/4812; A61B 5/1128; A61B 5/4809; A61B 2560/0223; A61B 5/0077; B60W 60/00; B60W 2540/229; B60W 2040/0872; B60W 2420/40; B60W 2540/221; G06V 10/774; G06V 20/597
See application file for complete search history.

(56) References Cited

U.S. PATENT DOCUMENTS

| | | | | |
|---|---|---|---|---|
| 2010/0079294 | A1* | 4/2010 | Rai | A61B 5/18 340/575 |
| 2010/0090839 | A1 | 4/2010 | Omi | |
| 2012/0133515 | A1 | 5/2012 | Palshof | |
| 2014/0046546 | A1 | 2/2014 | Kollegger et al. | |
| 2016/0071393 | A1 | 3/2016 | Kaplan et al. | |
| 2017/0313190 | A1* | 11/2017 | Shimada | G16H 40/67 |
| 2019/0216391 | A1* | 7/2019 | Kenyon | G16H 50/30 |
| 2020/0317211 | A1 | 10/2020 | Stiller et al. | |
| 2022/0375590 | A1* | 11/2022 | Kinnunen | A61B 5/742 |
| 2023/0245474 | A1* | 8/2023 | Shinozaki | A61B 5/7267 382/103 |
| 2024/0199061 | A1 | 6/2024 | Reifman | |

OTHER PUBLICATIONS

Perkins et al., "Challenges of Driver Drowsiness Prediction: The Remaining Steps to Implementation", in IEEE Transactions on Intelligent Vehicles, vol. 8, No. 2, pp. 1319-1338, Feb. 2023 (Year: 2023).*

Riani et al., "Towards Classifying Human Circadian Rhythm Using Multiple Modalities," 2021 9th International Conference on Affective Computing and Intelligent Interaction (ACII), Nara, Japan, 2021, pp. 1-8 (Year: 2021).*

Shraddha et al., "Driver Drowsiness Detection System Using Artificial Intelligence", 2023 International Conference on Computing, Communication, and Intelligent Systems (ICCCIS), pp. 1183-1188 (Year: 2023).*

Reddy et al., "Effective Model of Detecting Driver's Drowsiness", Proceedings of the 5th International Conference on Smart Systems and Inventive Technology (ICSSIT 2023), pp. 1405-1408 (Year: 2023).*

"Taxonomy and Definitions for Terms Related to Driving Automation Systems for On-Road Motor Vehicles", National Highway Traffic Safety Administration (NHTSA), A Division of the US Department of Transportation, and the Society of Automotive Engineers (SAE), Standard No. J3016-201609, pp. 1-30 (Sep. 30, 2016).

"Taxonomy and Definitions for Terms Related to Driving Automation Systems for On-Road Motor Vehicles", National Highway Traffic Safety Administration (NHTSA), A Division of the US Department of Transportation, and the Society of Automotive Engineers (SAE), Standard No. J3016-201806, Jun. 15, 2018, pp. 1-35.

'ISO 26262, "Road vehicle—Functional safety," International standard for functional safety of electronic system, Retrieved from Internet URL: https://en.wikipedia.org/wiki/ISO_26262, accessed on Sep. 13, 2021, 8 pages.

"Circadian Rhythms Promote Wakefulness", Centers for Disease Control and Prevention, Retrieved on Apr. 1, 2020, 1 page.

"Circadian Rhythms", National Institute of General Medical Sciences, Oct. 2020, 3 pages.

De Naurois et al., "Detection and Prediction of Driver Drowsiness Using Artificial Neural Network Models", Accident Analysis & Prevention, vol. 126, May 2019, pp. 95-104.

Ghoddoosian et al., "A Realistic Dataset and Baseline Temporal Model for Early Drowsiness Detection", 2019 IEEE/CVF Conference on Computer Vision and Pattern Recognition Workshops (CVPRW), 2019, 10 pages.

IEC 61508, "Functional Safety of Electrical/Electronic/Programmable Electronic Safety-related Systems," Retrieved from Internet URL: https://en.wikipedia.org/wiki/IEC_61508, accessed on Apr. 1, 2022, 7 pages.

Massoz et al., "The ULg Multimodality Drowsiness Database (called Drozy) and Examples of Use", 2016 IEEE Winter Conference on Applications of Computer Vision (WACV), May 2016, 7 pages.

Shahid et al., "Karolinska Sleepiness Scale", Stop, That and One Hundred Other Sleep Scales, 2012, pp. 209-210.

Non-Final Office Action received for U.S. Appl. No. 18/408,336, mailed on Jan. 23, 2026, 16 pages.

Notice of Allowance received for U.S. Appl. No. 18/408,336, mailed on May 26, 2026, 8 pages.

* cited by examiner

RECEIVE A FIRST GROUND TRUTH IMAGE SEQUENCE REPRESENTING VISUAL CHARACTERISTICS OF A TEST SUBJECT IN THE FIRST GROUND TRUTH IMAGE SEQUENCE DURING A TESTING PERIOD, THE FIRST GROUND TRUTH IMAGE SEQUENCE COMPRISING ONE OR MORE DROWSINESS LABELS INDICATING A DROWSINESS OF THE TEST SUBJECT
B602

CORRELATE A POSITION ON A CIRCADIAN RHYTHM PROCESS TO A TIME OF THE TESTING PERIOD
B604

APPLY ONE OR MORE DROWSINESS CORRECTIONS TO THE ONE OR MORE DROWSINESS LABELS BASED AT LEAST ON AN ALERTNESS VALUE CORRESPONDING TO THE POSITION ON THE CIRCADIAN RHYTHM PROCESS, TO GENERATE A SECOND GROUND TRUTH IMAGE SEQUENCE
B606

TRAIN A MACHINE LEARNING MODEL TO INFER A DROWSINESS LEVEL BASED ON THE SECOND GROUND TRUTH IMAGE SEQUENCE
B608

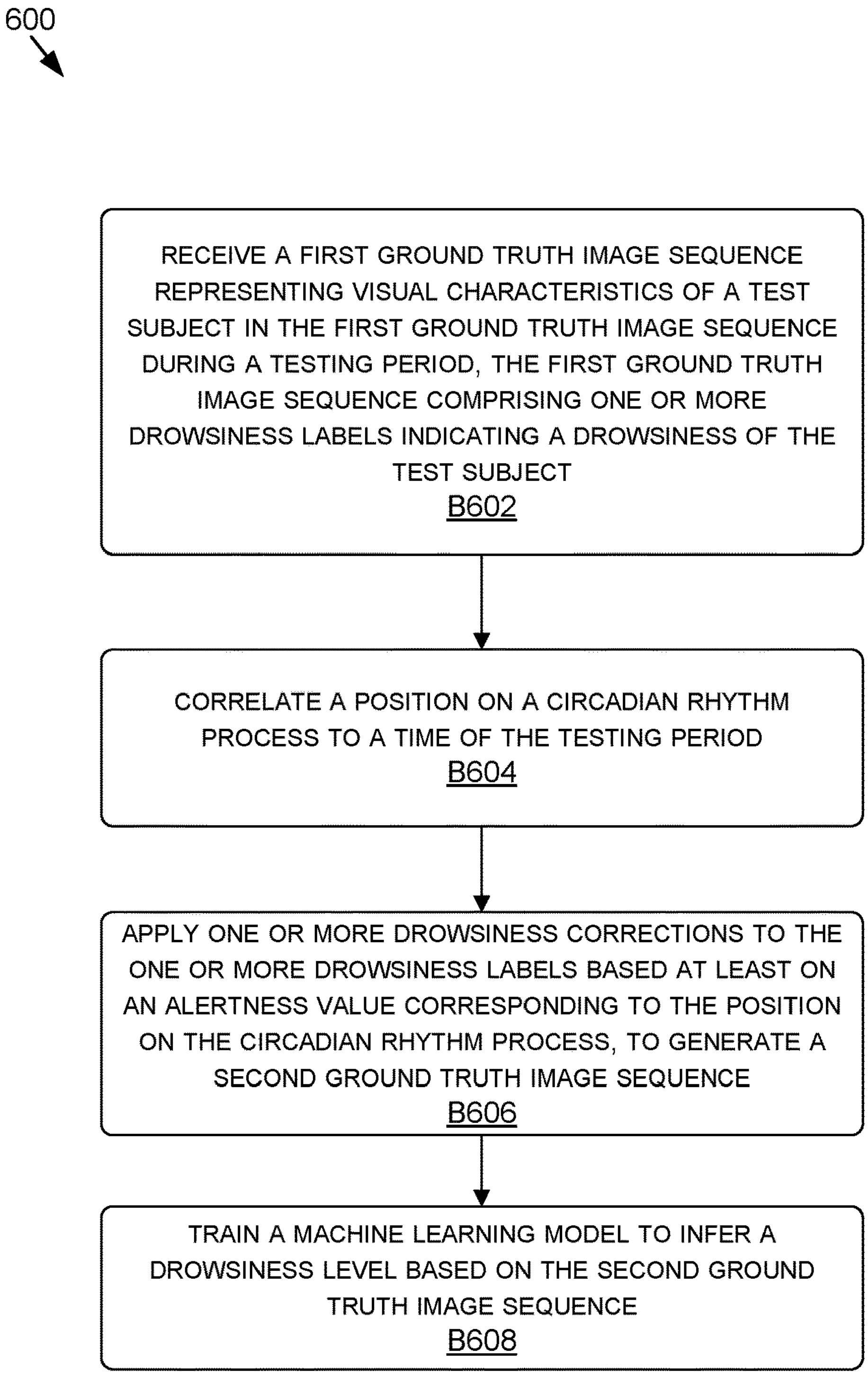

FIGURE 6

SERVER(S) 878

CPU 880(A)

CPU 880(B)

PCIe SWITCH 882(A)

PCIe SWITCH 882(B)

PCIe SWITCH 882(C)

PCIe SWITCH 882(D)

886

GPU 884(A)

GPU 884(B)

GPU 884(C)

GPU 884(D)

GPU 884(E)

GPU 884(F)

GPU 884(G)

GPU 884(H)

888

NETWORK(S) 890

892

894

800

CIRCADIAN RHYTHM-BASED TRAINING DATA CORRECTION FOR DROWSINESS DETECTION SYSTEMS AND APPLICATIONS

CROSS-REFERENCE TO RELATED APPLICATIONS

This application is related to U.S. patent application Ser. No. 18/408,336 titled, "CIRCADIAN RHYTHM-BASED DATA AUGMENTATION FOR OCCUPANT STATE ANALYSIS", filed on Jan. 9, 2024, which is incorporated herein by reference in its entirety.

BACKGROUND

Vehicle accidents can occur when the driver of a vehicle is too drowsy to operate the vehicle safely. Driver drowsiness detection technologies are safety features available today in many vehicles. These technologies can take various forms of sensor inputs to estimate driver alertness versus drowsiness, and alert the driver to warn them when drowsiness is reaching a level that may inhibit safe operation of the vehicle. Applied in various ways, these technologies can estimate driver alertness using vision-based techniques (e.g., observing eye movements, yawning, or nodding), driver interactions with the steering wheel, and/or technologies that monitor vehicle behaviors, such as lane-keeping, for example. Driver drowsiness detection technologies are typically included in vehicles featuring Advanced Driver Assistance Systems (ADAS).

SUMMARY

Embodiments of the present disclosure relate to circadian rhythm-based data augmentation for drowsiness detection systems and applications. Systems and methods are disclosed that incorporate occupant circadian rhythm data to augment vision-based assessments of human drowsiness.

In contrast to conventional systems, embodiments described herein may produce an estimated circadian rhythm for a test subject and/or vehicle driver, and use the pattern of that circadian rhythm to correct, confirm, calibrate, or otherwise augment drowsiness assessments derived from image sensor data (such as video frame sequences). Of particular relevance to human alertness and drowsiness levels is the circadian rhythm known as process C, which promotes sleepiness in the evenings before typical bedtimes, and promotes wakefulness in the morning when it is typically time for a person to wake up. As such, the position of a person in the context of their process C circadian cycle can be an indication of their level of drowsiness. An estimated process C circadian cycle may be used early in the process of developing drowsiness detection to generate more accurate ground truth training data for training machine learning models. For example, a circadian rhythm-based drowsiness level may be estimated for a test subject to correct and/or replace human-assessed drowsiness levels that are reported while capturing video imagery of the test subject. In some embodiments, estimated process C circadian rhythm may separately be used by real-time, in-vehicle drowsiness detection systems that infer driver drowsiness levels based on captured images. For example, a circadian rhythm-based drowsiness estimate may be used to correct and/or discard potentially inaccurate drowsiness scores inferred by a machine learning model from image data of a driver or other occupant of a vehicle or (e.g., heavy) machine. A circadian rhythm drowsiness estimate for a driver may comprise a drowsiness score derived from estimating the position of the vehicle driver with respect to their circadian rhythm process C curve. That position on the process C curve may be estimated based on the current time of day, and may be further refined based on additional information about the timing, quality of the driver's recent sleep, time on the task, and/or similar information. In various embodiments, a circadian rhythm drowsiness estimate may be used to correct, calibrate, augment, and/or replace a drowsiness score predicted by the machine learning model.

BRIEF DESCRIPTION OF THE DRAWINGS

The present systems and methods for circadian rhythm-based data augmentation for drowsiness detection are described in detail below with reference to the attached drawing figures, wherein:

FIG. 6 is a flow diagram for a method for circadian rhythm-based ground truth correction, in accordance with some embodiments of the present disclosure;

DETAILED DESCRIPTION

Figure 1:
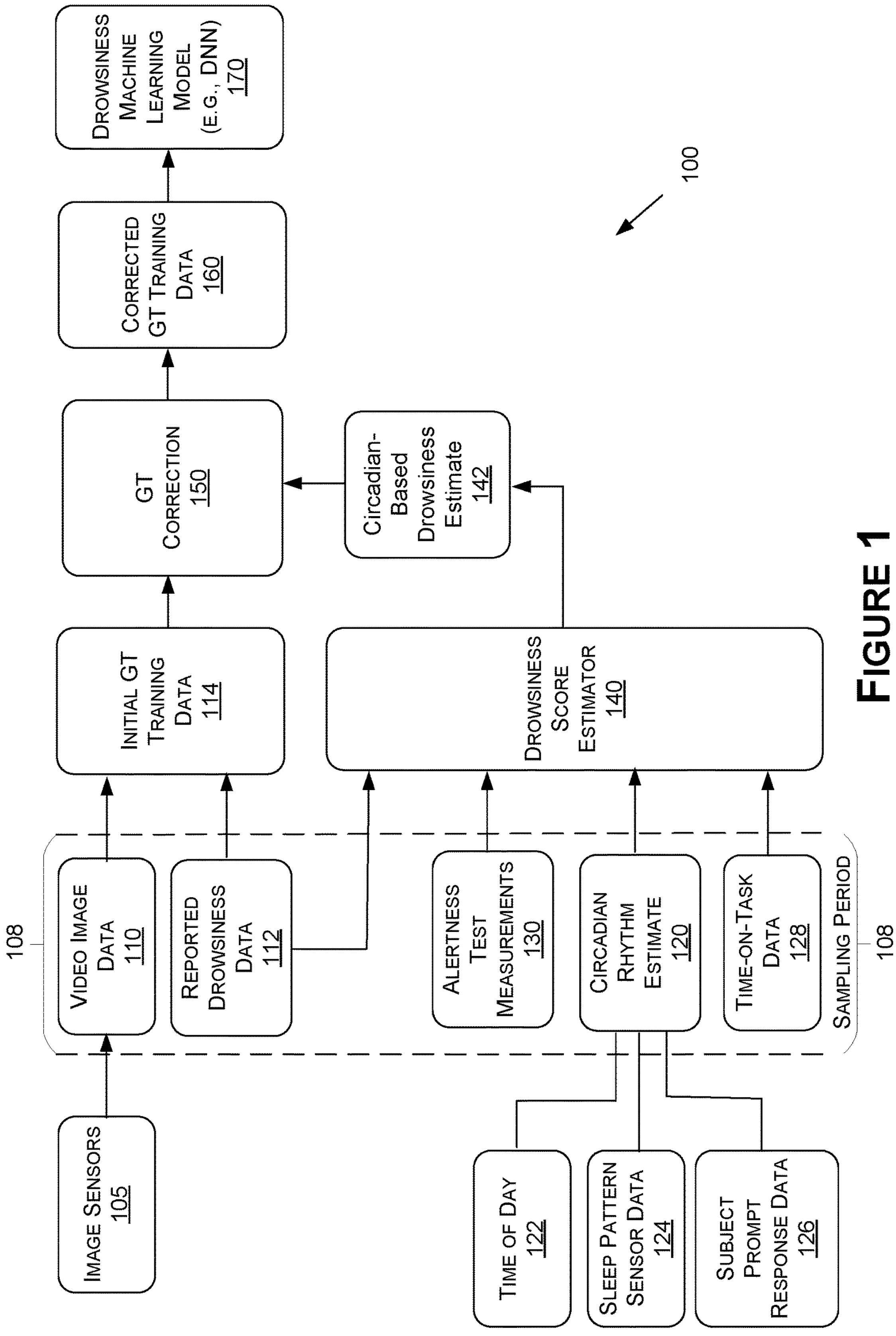
FIG. 1 is a data flow diagram for a circadian rhythm-based ground truth correction system, in accordance with some embodiments of the present disclosure.

Systems and methods are disclosed related to circadian rhythm-based data augmentation for drowsiness detection systems and applications. Although the present disclosure may be described with respect to an example autonomous or semi-autonomous vehicle or machine 800 (alternatively referred to herein as "vehicle 800" or "ego-machine 800," an example of which is described with respect to FIGS. 8A-8D), this is not intended to be limiting. For example, the systems and methods described herein may be used by, without limitation, non-autonomous vehicles or machines, semi-autonomous vehicles or machines (e.g., in one or more advanced driver assistance systems (ADAS)), autonomous vehicles or machines, piloted and un-piloted robots or robotic platforms, warehouse vehicles, off-road vehicles, vehicles coupled to one or more trailers, flying vessels, boats, shuttles, emergency response vehicles, motorcycles, electric or motorized bicycles, aircraft, construction vehicles, trains, underwater craft, remotely operated vehicles such as drones, and/or other vehicle types. In addition, although the present disclosure may be described with respect to drowsiness detection for vehicle drivers and/or machine operators, this is not intended to be limiting, and the systems and methods described herein may be used in augmented reality, virtual reality, mixed reality, robotics, security and surveillance, autonomous or semi-autonomous machine applications, and/or any other technology spaces where drowsiness detection may be used.

The present disclosure relates to circadian rhythm-based data augmentation for drowsiness detection systems and applications. As discussed herein, systems and methods are provided that incorporate human circadian rhythm data to augment vision-based assessments of human drowsiness.

Drowsiness detection systems today often use computer vision and deep learning techniques to monitor observable manifestations of a driver's physiological state, such as their eye blinking pattern, their posture or gaze, or their ability to control the vehicle (e.g., lane-keeping) to derive a score representing the driver's drowsiness. For example, in-cabin cameras may detect a longer-duration eye closure and/or slow versus fast blink rate, and estimate a drowsiness level of the driver based on those factors. However, there are factors that can cause inaccuracies in drowsiness estimates based solely on computer vision. For example, the ability to view the driver's eyes may be partially occluded, for example by glasses, a hat, or a visor, worn by the driver, or due to driver head motion. Similarly, conditions may make it difficult to capture images of lane markings, or lane markings may be worn or absent for a given stretch of roadway. Moreover, the labeling of ground truth data used for training machine learning-based drowsiness detection systems can be biased due to the subjective nature of a training subject's ability to accurately self-assess and report their own drowsiness, or even when trained observers are used to assess and report the training subject's drowsiness.

In contrast to these traditional technologies for drowsiness detection, one or more of the embodiments described herein incorporate circadian rhythm data to augment image-based assessments of human drowsiness. Circadian rhythm is an internal twenty-four hour biological clock that regulates physiological processes in human beings, including sleep-wake patterns that affect drowsiness, wakefulness, alertness, and sleepiness. While circadian rhythm roughly follows a twenty-four cycle, that cycle can be influenced by external cues such as the person's exposure to light and darkness and/or their typical daily work schedule (e.g., if they perform shift work). Of particular relevance to human alertness and drowsiness levels is the circadian rhythm known as process C, which promotes sleepiness in the evenings before typical bedtimes, and promotes wakefulness in the morning when it is typically time for a person to wake-up. As such, a typical process C cycle might begin to increase wakefulness in the morning (e.g., around 7:00 am) and support alertness through the day, but then decrease wakefulness starting in the early evening (e.g., around 5:00 pm) to increase drowsiness and promote a restful sleep cycle until the following morning. As such, the position of a person in the context of their process C circadian cycle can be an indication of their level of drowsiness. As discussed herein, some embodiments may produce an estimated process C circadian rhythm for a test subject and/or vehicle driver, and use the pattern of that estimated process C circadian rhythm to correct, confirm, calibrate, or otherwise augment drowsiness assessments derived from image sensor data (such as video frame sequences). In some embodiments, the image sensor data may be obtained from optical image sensors such as, but not limited to, a camera or other optical sensor that captures, as non-limiting examples, RGB, infrared (IR), and/or RGB-IR image frames.

As described herein, estimated process C circadian rhythm may be used early in the process of developing drowsiness detection to generate more accurate ground truth training data for training machine learning models, as compared to ground truth training data that relies on test subjects accurately self-reporting their drowsiness. Estimated process C circadian rhythm may separately be used by real-time, in-vehicle drowsiness detection systems that infer driver drowsiness levels based on captured images.

Regarding the use of estimated process C circadian rhythm to produce ground truth training data, a circadian rhythm-based drowsiness may be estimated for a test subject to correct and/or replace human-assessed drowsiness levels that are reported while capturing video imagery of the test subject. For example, in some embodiments, collection of training data from test subjects (e.g., human subjects used for collecting training data) may comprise the test subject performing a series of psychomotor vigilance tests (PVTs) over the course of a testing period that may span, for example, one or more days. The test subject may be permitted an initial normal sleep period, but is then subject to sleep deprivation during the remaining portion of the testing period during which the PVTs are performed. The PVTs can be tests performed to assess changes in the alertness level of the test subject associated with extended periods of lack of sleep. For example, during a PVT session, the test subject may be instructed to respond to a visual stimulus, for example, to push a button in response to an illumination of a light or a graphic on a display screen. An indication of drowsiness may be derived based on the number of times the test subject fails to respond (e.g., push the button) when the visual stimulus is presented and/or the time duration the test subject takes to respond to the visual stimulus. At different points during the PVT, the test subject may be asked to report how drowsy they feel, and/or one or more trained observers may record how drowsy they judge the test subject to be. Drowsiness can be reported using the Karolinska Sleepiness Scale (KSS), in which situational sleepiness is recorded using a 9-point scale (e.g., where 1=extremely alert, 2=very alert, 3=alert, 4=rather alert, 5=neither alert nor sleepy, 6=some signs of sleepiness, 7=sleepy, but no effort to keep awake, 8=sleepy, some effort to keep awake, and 9=very sleepy, great effort keeping awake, fighting sleep). The ability of the test subject to properly respond to visual stimuli may provide rough correlation data to validate the reported drowsiness by the test subject and/or the observer. To obtain video data that can be used for training a machine learning model (e.g., a drowsiness detection deep neural network (DNN)) video of the test subject's head and face can be recorded during the PVT sessions. The observed drowsiness levels can be correlated in time with the recorded video in order to label sequences of frames of captured video with reported drowsiness levels. However, training data labels that heavily rely on reported drowsiness levels (whether self-reported or from independent observers) is inherently limited with respect to reliability and may include mislabeling due to judgement errors, inaccurate recording of reported drowsiness levels, or other factors.

To address these challenges, in some embodiments, an estimated process C circadian rhythm for the test subject may be used to generate corrections to the labeled sequences of video frames obtained during the PVT session and/or assign a confidence to the drowsiness levels indicated by the labels attached to the video sequences. Based on the corrections, a corrected ground truth training data set may be generated for training machine learning models. For example, a circadian rhythm estimate may be determined by estimating a position on a process C curve where the test subject is, for example, based on a time of day and/or how long it has been since the test subject last woke from sleep. A corresponding expected drowsiness level derived from the process C curve can be compared to the drowsiness level from a labeled sequence of video frames captured at that time. In some embodiments, a corrected ground truth training data sample can be produced, for example, using a weighted smoothing algorithm that smooths sudden changes in the reported drowsiness level from a labeled sequence of video frames and/or averages differences between expected drowsiness from the process C curve and the reported drowsiness level. In some embodiments, sensor data may be used to estimate the process C circadian rhythm for the test subject and where they are on the process C curve. For example, in some embodiments, the test subject may wear a sensor (e.g., on a wearable device) that records sleep data from the test subject's prior sleep period to quantify metrics that characterize the quality of the test subject's last sleep and/or the time they awoke. In some embodiments, the test subject may be prompted to answer a series of questions to assist in estimation where they are with respect to their process C circadian rhythm. For example, the test subject may be asked what time they last woke up from sleep, asked about the quality of their sleep, and/or if they've consumed any stimulants (e.g., coffee). Based on such sleep data, the test subject's initial position on the process C curve at the time of a PVT session can be more accurately established to obtain a more accurate corresponding expected drowsiness level from the process C curve to compare against, and correct, the labeled drowsiness levels for the sequence of video frames.

As previously mentioned, the cycle of the circadian rhythm can be influenced by external factors. One such factor that can affect the circadian rhythm cycle is mental fatigue caused by performing a particular task for extended periods of time. During a long drive, for example, circadian rhythm may be influenced by the duration of the drive. As such, in some embodiments, the ground truth data correction may be adjusted based on the combination of the expected drowsiness level derived from the process C curve and further based on time-on-task data. Time-on-task data may be computed as a function of the amount of time the test subject has been in a PVT session and/or the amount of time the test subject has been actively performing mental tasks within the testing period since the initial normal sleep period. For example, a histogram of drowsiness level versus time of task may be generated and the expected drowsiness level derived from the process C curve increased as a function of the histogram. Other alertness data, such as test measurements, may also, or instead, be used to adjust the expected drowsiness level derived from the process C curve. For example, mean reaction time (MRT) measurements obtained during a PVT session based on response times to push a button after receiving a visual stimulus may be factored into computation of the ground truth data correction. As another example, in some embodiments, during PVT sessions where ground truth data is collected, the test subject can be monitored using sensors that measure brain activity. For example, sensors may be attached to the scalp of the test subject to perform an electroencephalogram (EEG) test during PVT sessions to measure associated brain waves that vary with alertness versus drowsiness. The brain wave activity may be translated to a drowsiness level that is used to adjust the expected drowsiness level derived from the process C curve or otherwise factored into computation of the ground truth data correction. Other external factors influencing the process C curve can include sudden road events (e.g., such as the appearance of an animal on the road) that may wake up a drowsy driver which may increase the driver's alertness level for at least a short period of time.

In some embodiments, the ground truth data correction can be computed for each of the PVT sessions and used to correct the initial drowsiness level labels applied to the initial ground truth video image data. The corrected ground truth training data may then be used in processes to train machine learning models to detect drowsiness. For example, the corrected ground truth training data may include one or more image sequences of the head and/or face of a test subject. The machine learning models may input the image sequences and infer a person's drowsiness based on features observable from the image sequence such as blink rate, blink velocity, blink amplitude, time of eye closure, head pose (e.g., upright versus slouched), eye gaze patterns (e.g., where the subject's eyes are gazing), yawning patterns, and/or other observable parameters that evidence drowsiness. Drowsiness level predictions inferred by the machine learning models may be compared to the corrected drowsiness labels derived from the estimated process C circadian rhythm to generate a loss feedback for adjusting the machine learning model (e.g., as a function of how well the machine learning model predictions correspond with the test subject's drowsiness levels indicated by corrected drowsiness labels).

As mentioned above, in some embodiments, estimated drowsiness based on circadian rhythm may be used by real-time drowsiness detection systems that infer vehicle operator drowsiness levels based on captured image data. The resulting drowsiness score output from the real-time drowsiness detection system may represent drowsiness using a standardized drowsiness score scale, such as KSS drowsiness score values. Based on the drowsiness score output, one or more safety operations may be triggered, such as audio and/or visual warnings that may be used to stimulate the driver's alertness, advise the driver to pull over and stop the vehicle, and/or alert other occupants in the vehicle of the driver's drowsiness. In some embodiments, automated actions in response to driver drowsiness may be tiered based on the driver's level of drowsiness. In some embodiments, the real-time drowsiness detection system may also operate using a tiered system where drowsiness score outputs are generated less frequently when drowsiness scores are low (e.g., the driver appears less drowsy) and more frequently when drowsiness scores are high (e.g., the driver appears more drowsy).

A circadian rhythm-based drowsiness estimate may be used to correct and/or discard potentially inaccurate drowsiness scores inferred by a machine learning model from driver image data. For example, when a driver has been operating a vehicle for several hours, their level of drowsiness may, over the course of the drive, vary depending on where they are with respect to their circadian rhythm. A machine learning model that is accurately inferring a drowsiness score for the driver would be expected to generate drowsiness scores that gradually change over time over the course of the drive, but are not expected to change substantially (e.g., more than one KSS level) from one prediction to the next. Accordingly, if an inferred drowsiness score prediction from the machine learning model does change more than a threshold value over a series of predictions, the circadian rhythm drowsiness estimate may be used to replace the anomalous drowsiness scores from the machine learning model.

A circadian rhythm drowsiness estimate may comprise a drowsiness score derived from estimating the position of the vehicle driver with respect to their circadian rhythm process C curve. That position on the process C curve may be estimated based on the current time of day, and may be further refined based on additional information about the timing and/or quality of the driver's recent sleep. For example, when a driver enters the vehicle, they may be prompted to answer a series of questions such as, but not limited to, what time they last woke up from sleep, the quality of their sleep, and/or if they've consumed any stimulants (e.g., coffee), and the like. Based on the answers to the driver prompts, a drowsiness detection system may compute an estimation of where they are with respect to their process C curve at the time they begin to operate the vehicle, and adjust and track that position during the drive based on time of day. In some embodiments, the vehicle operator may wear one or more sensors (e.g., on a wearable device) that records sleep data from the driver's prior sleep period to quantify metrics that characterize the quality of the test subject's last sleep and/or the time they awoke, or measure other body signals. This sleep data may be uploaded to the drowsiness detection system as the driver begins operation of the vehicle and may be used to compute an estimation of where they are with respect to their process C curve at the time they begin to operate the vehicle, and adjust and track that position during the drive based on time of day. In some embodiments, the drowsiness detection system may compute, and weigh into circadian rhythm drowsiness estimates, a time-on-task factor that further accounts for fatigue resulting from the time the driver has been operating the vehicle.

In some embodiments, a circadian rhythm drowsiness estimate may be combined with a drowsiness score inferred by a machine learning model, for example, using a weighted sum. That is, the machine learning model may infer a first drowsiness level estimated based on captured images, while a second drowsiness level is computed based at least on an estimation of where the vehicle operator is with respect to their circadian rhythm process C curve. An estimate fusing function, such as an averaging algorithm, smoothing algorithm, or similar algorithm may be used to fuse and/or combine the first and second drowsiness estimates. As discussed above, drowsiness scores are expected to gradually change over time over the course of a drive, and not expected to change substantially from one prediction to the next. Accordingly, in some embodiments, the estimate fusing function may average or otherwise statistically combine the circadian rhythm drowsiness estimate and the inferred drowsiness score to compute the drowsiness score output. For example, in some embodiments, the estimate fusing function may compute a rate of change at the driver's current location on the circadian rhythm process C curve and apply that rate of change to a prior inferred drowsiness score to compute a correction to a current inferred drowsiness score. The combined drowsiness score may then be used as the basis for a drowsiness score output from the real-time drowsiness detection system.

In some embodiments, a circadian rhythm drowsiness estimate may be used to calibrate inputs to a machine learning model of the real-time drowsiness detection system so that the model predicts driver drowsiness levels more accurately. For example, training of the machine learning model may be based on ground truth training data that comprises images of hundreds or thousands of test subjects over a wide demographic spectrum. In contrast, a production machine learning model may in practice be used to predict and/or track drowsiness for just a small handful of people over the lifetime of a vehicle. As such, in some embodiments a circadian rhythm process C curve may be calibrated to an individual driver, and a circadian rhythm drowsiness estimate baseline for the driver established at the time of calibration. The circadian rhythm drowsiness estimate baseline may then be associated with an observable indicia of drowsiness derived from the captured image data so that the machine learning model can further incorporate personal driver data from which it can produce a more accurate inferred drowsiness score based on captured image data of the driver.

For example, each vehicle driver may have personal observable physiological patterns with respect to drowsiness. As an example, different drivers may vary in terms of their blinking patterns (e.g., how they blink regularly when they are alert versus drowsy) and with respect to how other indicia of drowsiness are manifested physiologically. In some embodiments, when a driver assumes operation of a vehicle, their initial position on the process C curve at that time can be estimated as described above (e.g., based on time of day, sensor data, response to prompts, and the like). Based on that initial position on the process C curve, a corresponding expected drowsiness level may be derived and associated with the driver's current blinking pattern behaviors. That correlation may be stored into memory as a personal calibration parameter that may be recalled for use in the future. The personal calibration parameter may be used as a supplemental input to the drowsiness detection machine learning model, along with the captured image data from the driver. As an example, at the time of calibration a driver may be observed as having a blink rate of 22 blinks per minute while the circadian rhythm drowsiness estimate for the driver at the time of calibration indicates that they are alert (e.g., a KSS score of 3). One or more calibration parameters, based on that correlation, may be computed that comprise an offset, bias, or other operator calibration data that the machine learning model may use to shift its drowsiness score predictions when that driver is operating the vehicle. In some embodiments, such calibration parameters for different drivers may be stored to memory and recalled based on recognizing a driver as having previously saved calibration parameters (e.g., based on voice recognition, facial recognition, and/or an identifier provided by a key fob or wearable device). Calibration parameters associated with a driver may be maintained as valid for a prescribed period of time (e.g., 8 hours, 24 hours, the length of a driving session allowing for breaks of limited duration) and recomputed once the prescribed period of time has expired.

It should be appreciated that the embodiments described herein may be used in the context of real-time drowsiness systems to assess the drowsiness level of a vehicle operator (e.g., a driver or an automobile, an engineer of a train, and/or a pilot of an aircraft, spacecraft and/or boat), but may be extended to assess the drowsiness level of an operator of other machinery such as remote-operated devices (e.g., robots and drones), industrial and/or heavy machinery (e.g., lifts and cranes), and/or any other application where drowsiness may adversely affect the operator of a machine.

With reference to FIG. 1, FIG. 1 is an example data flow diagram for a circadian rhythm-based ground truth correction system 100, in accordance with some embodiments of the present disclosure. It should be understood that this and other arrangements described herein are set forth only as examples. Other arrangements and elements (e.g., machines, interfaces, functions, orders, groupings of functions, etc.) may be used in addition to or instead of those shown, and some elements may be omitted altogether. Further, many of the elements described herein are functional entities that may be implemented as discrete or distributed components or in conjunction with other components, and in any suitable combination and location. Various functions described herein as being performed by entities may be carried out by hardware, firmware, and/or software. For instance, various functions may be carried out by a processor executing instructions stored in memory. In some embodiments, the systems, methods, and processes described herein may be executed using similar components, features, and/or functionalities to those of example autonomous vehicle 800 of FIGS. 8A-8D, example computing device 900 of FIG. 9, and/or example data center 1000 of FIG. 10.

As shown in FIG. 1, circadian rhythm-based ground truth correction system 100 may comprise a ground truth (GT) correction function 150 that receives initial GT training data 114 and a circadian rhythm-based drowsiness estimate 142, and from those inputs, generates corrected GT training data 160. Initial GT training data 114 may include video image data 110 and reported drowsiness data 112 that were captured contemporaneously during a ground truth sampling period 108.

In some embodiments, video image data 110 may be obtained from one or more image sensors 105 that capture video (e.g., sequences of image frames) of a test subject's head and face during the ground truth sampling period 108. The image sensor(s) 105 may comprise, for example, a camera or other optical sensor that captures, as non-limiting examples, RGB, IR, and/or RGB-IR image frames to generate video image data 110. Reported drowsiness data 112 may include a self-reported drowsiness level from the test subject, and/or a drowsiness level estimated by a trained observer who is watching the test subject for indications of the test subject's level of drowsiness. Drowsiness can be reported (by the test subject and/or the observer) using a standardized scale, such as the Karolinska Sleepiness Scale (KSS). Using the KSS, situational sleepiness may be reported for the test subject using a 9 point scale, for example where 1=extremely alert, 2=very alert, 3=alert, 4=rather alert, 5=neither alert nor sleepy, 6=some signs of sleepiness, 7=sleepy, but no effort to keep awake, 8=sleepy, some effort to keep awake, and 9=very sleepy, great effort keeping awake, fighting sleep. Sequences of the video image frames of the video image data 110 captured during the ground truth sampling period 108 may be labeled based on the reported drowsiness data 112 so that the initial GT training data 114 includes video images of the test subject along with an associated level of the drowsiness of the test subject at the time the video images were captured. In some embodiments, video image data 110 and reported drowsiness data 112 may be aligned in time, for example using time stamps, to produce the initial GT training data 114.

In some embodiments, collection of the video image data 110 and reported drowsiness data 112 may be captured while the test subject is performing one or more tasks during the ground truth sampling period 108. For example, in some embodiments, the test subject may perform a series of psychomotor vigilance tests (PVTs) over the course of the ground truth sampling period 108. The PVTs can be tests performed to assess changes in the alertness level of the test subject associated with extended periods of lack of sleep. At different points during the PVT, the test subject may be asked to self-report how drowsy they feel, and/or one or more trained observers may record how drowsy they judge the test subject to obtain the reported drowsiness data 112 for producing training data labels for the video image data 110.

As mentioned above, because reported drowsiness data 112 is produced based on assessments performed and recorded by a human being, it may be inherently limited with respect to reliability and may include mislabeling due to judgement errors, accurate recording of reported drowsiness levels, or other factors. As such, the circadian rhythm-based ground truth correction system 100 of FIG. 1 generates a circadian-based drowsiness estimate 142 that can be used to augment the initial GT training data 114 by correcting and/or replacing training data labels derived from the reported drowsiness data 112. More specifically, the circadian rhythm-based ground truth correction system 100 uses a circadian rhythm estimate 120 to produce an assessment of circadian-based alertness. The circadian-based alertness is an assessment of the alertness of the test subject based on an estimate of where the test subject is with respect to their circadian rhythm cycle. This assessment may be input to a drowsiness score estimator 140 that produces the circadian-based drowsiness estimate 142 used to correct the initial GT training data 114.

Figure 2:
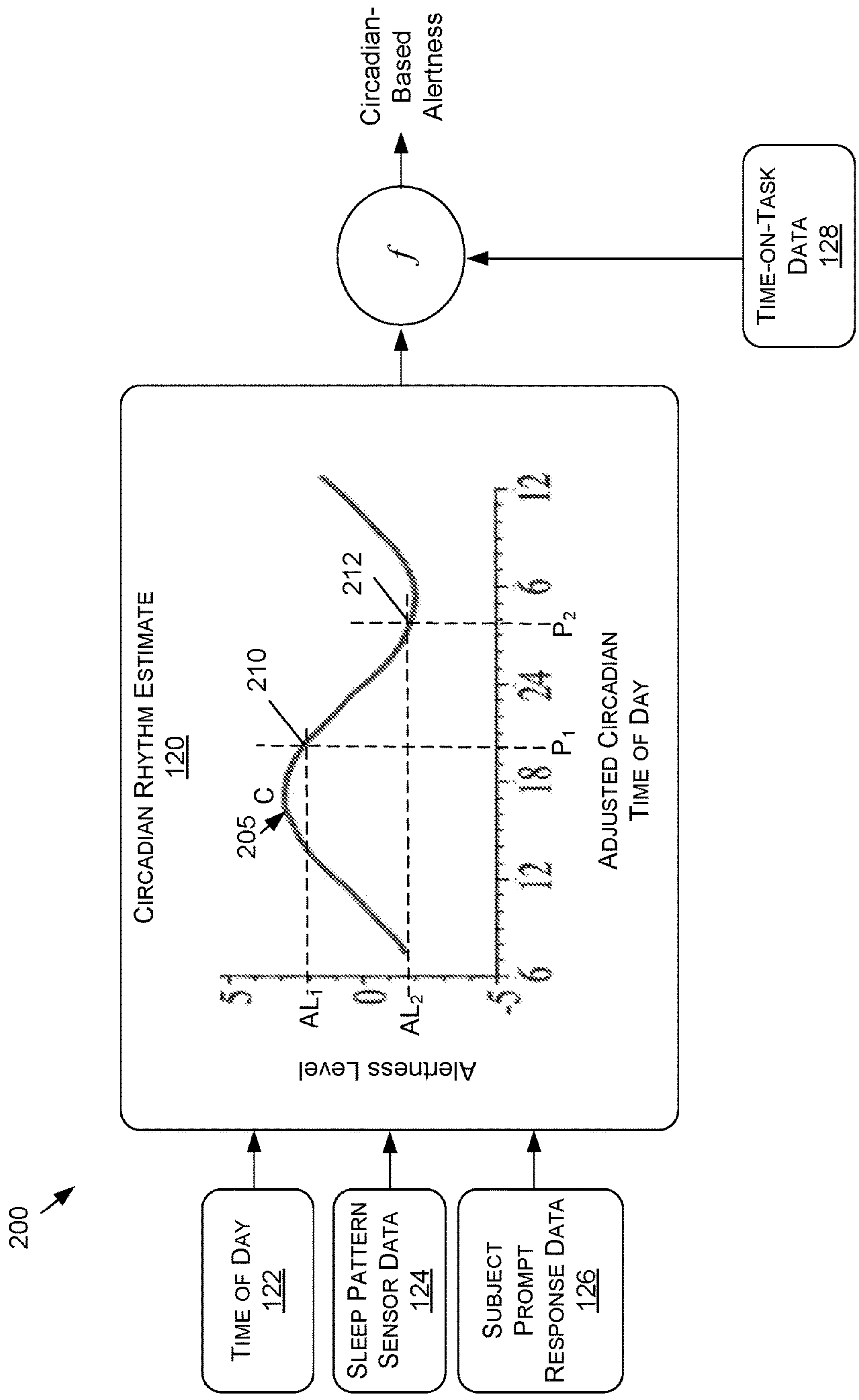
FIG. 2 is a data flow diagram that illustrates circadian-based alertness estimation, in accordance with some embodiments of the present disclosure.

For example, referring now to FIG. 2, FIG. 2 is a flow diagram illustrating circadian rhythm estimate 120 and computation of circadian-based alertness for a test subject. Of particular relevance to human alertness and drowsiness level is the Circadian rhythm know as process "C" represented in FIG. 2 as C-curve 205. A baseline process C cycle 205 might begin to increase wakefulness in the morning (e.g., around 7:00 am) and support alertness through the day, and then decrease wakefulness starting in the early evening (e.g., around 5:00 pm) to increase drowsiness and promote a restful sleep cycle until the following morning. For example, for a person at position $P_1$ along the time of day axis for the circadian rhythm estimate 120, the C-curve 205 may correlate to a first point 210 that indicates an alertness level of $AL_1$. For example, for a person at position $P_2$ along the time of day axis (e.g., later in the day from position $P_1$), the C-curve 205 may correlate to a second point 212 to indicate a relatively lower alertness level $AL_2$. Accordingly, in some embodiments, an alertness level for a test subject may be estimated based on an input representing the time of day 122, locating the position in the circadian rhythm cycle associated with that time of day 122 on the C-curve 205, and determining the corresponding alertness level from the value of the C-curve 205 at that position. Because the test subject's circadian rhythm cycle can be influenced by external cues such as the person's exposure to light and darkness, their typical daily work schedule (e.g., if they perform shift work), and or the quality of their recent sleep periods, in some embodiments, the test subject's position on the process C curve 205 may be further refined based on additional information about the timing and/or quality of the driver's recent sleep. For example, in some embodiments, the test subject may wear a sensor (e.g., on a wearable device) that records sleep data from the test subject's prior sleep period to produce sleep pattern data 124. Sleep pattern data 124 may include quantified metrics that characterize the quality of the test subject's last sleep and/or the time they awoke. In some embodiments the circadian rhythm estimate 120 may be adjusted or calibrated with respect to its time-of-day scale by an offset computed based on sleep quality or time they awoke. For example, if the test subject normally wakes up earlier than the defined nominal wake-up time for a process C curve 205 (e.g., they normally wake at 4:00 am rather than 7:00 am), then the process C curve 205 may be offset based on that 3-hour difference to calibrate it to the normal wake-up time of that test subject. As another example, if the time of day 122 indicates that it is 11:00 am but the sleep pattern data 124 indicates that the test subject woke up from their last sleep period eight hours ago, the circadian rhythm estimate 120 may be adjusted to position the subject further down the process C curve 205 based on the difference between the defined nominal wake-up time and the time the test subject actually awoke. In some embodiments, circadian rhythm estimate 120 may be adjusted or calibrated with respect to its time-of-day scale by an offset computed based on subject prompt response data 126. For example, the test subject may be asked what time they last woke up from sleep, asked about the quality of their sleep, and/or if they've consumed any stimulants (e.g., coffee). Based on such subject prompt response data 126, the test subject's initial position on the process C curve can be more accurately established from the circadian rhythm estimate 120 to obtain a more accurate corresponding expected drowsiness level from the process C curve 205. The alertness level established from the circadian rhythm estimate 120 may be used by the drowsiness score estimator 140 to convert the alertness level to the circadian-based drowsiness estimate 142 used to correct the initial GT training data 114.

As previously mentioned, another factor that can affect the process C curve 205 is mental fatigue caused by performing a particular task for extended periods of time. During a long drive, for example, circadian rhythm may be influenced by the duration on the drive such that the driver's alertness level diminishes more quickly towards sleepiness than may be reflected by the nominal process C curve 205. As such, in some embodiments, the circadian-based alertness level indicated by the circadian rhythm estimate 120 may be adjusted based on time-on-task data 128. Time-on-task data 128 may be computed as a function of the amount of time the test subject has been in a ground truth sampling period 108 session and/or the amount of time the test subject has been actively performing mental tasks within the testing period since the initial normal sleep period. For example, time-on-task data 128 may be computed based on a histogram of drowsiness level versus time on task and the expected alertness level derived from the process C curve 205 decreased as a function of the histogram. In some embodiments, the drowsiness score estimator 140 may receive a circadian-based alertness from the circadian rhythm estimate 120 and compute the adjustment to the circadian-based alertness based on the time-on-task data 128 to derive the circadian-based drowsiness estimate 142.

In some embodiments, the drowsiness score estimator 140 may adjust the circadian-based alertness using real-time objective alertness test measurements 130. For example, mean reaction time (MRT) measurements obtained during the ground truth sampling period 108 may be used by the drowsiness score estimator 140 to adjust the circadian-based drowsiness estimate 142. Such an MRT measurement may be based on response time for the test subject to push a button after receiving a visual stimulus, for example. As another example, in some embodiments, alertness test measurements 130 may include sensor data from sensors that monitor a test subject's heart rate, breathing pattern and/or brain activity. For example, sensors may be attached to the scalp of the test subject to perform an electroencephalogram (EEG) test during PVT sessions to measure associated brain waves that vary with alertness versus drowsiness. The brain wave activity may be translated by the drowsiness score estimator 140 to a drowsiness level that is used to adjust the circadian-based alertness from the circadian rhythm estimate 120 and produce the circadian rhythm-based drowsiness estimate 142.

As shown in FIG. 1, the ground truth (GT) correction function 150 that receives initial GT training data 114 and a circadian rhythm-based drowsiness estimate 142, and from those inputs, generates corrected GT training data 160. For example, in some embodiments, the GT correction function 150 may apply a weighted smoothing algorithm that smooths sudden changes in the reported drowsiness data 112 and/or averages differences between expected drowsiness from circadian rhythm-based drowsiness estimate 142 and the reported drowsiness data 112. The training data labels of the initial GT training data 114 may then be updated based on these corrections. In some embodiments, when a training data label of the initial GT training data 114 substantially deviates (e.g., by more than a predetermined threshold) from a drowsiness trend derived from the reported drowsiness data 112, the circadian rhythm-based drowsiness estimate 142 may be used by the GT correction function 150 to replace the anomalous training data label to produce the corrected GT training data 160.

The corrected ground truth training data 160 may then be used in processes to train a drowsiness machine learning model 170 to detect drowsiness. Such a drowsiness machine learning model 170 may include a drowsiness detection deep neural network (DNN). The drowsiness machine learning model 170 may input corrected ground truth training data 160 and infer the test subject's drowsiness based on features observable from an image sequence such as blink rate, blink velocity, blink amplitude, time of eye closure, head pose (e.g., upright versus slouched), eye gaze patterns (e.g., where the subject's eyes are gazing), yawning patterns, and/or other observable parameters that evidence drowsiness. The drowsiness machine learning model 170 may generate drowsiness level predictions, for example, that represent drowsiness of the test subject using the KSS. Drowsiness level predictions inferred during training of the drowsiness machine learning model 170 may be compared to the corrected drowsiness labels of the corrected ground truth training data 160 to generate a loss feedback for adjusting the drowsiness machine learning model 170 to improve the accuracy of its drowsiness level predictions.

Figure 3:
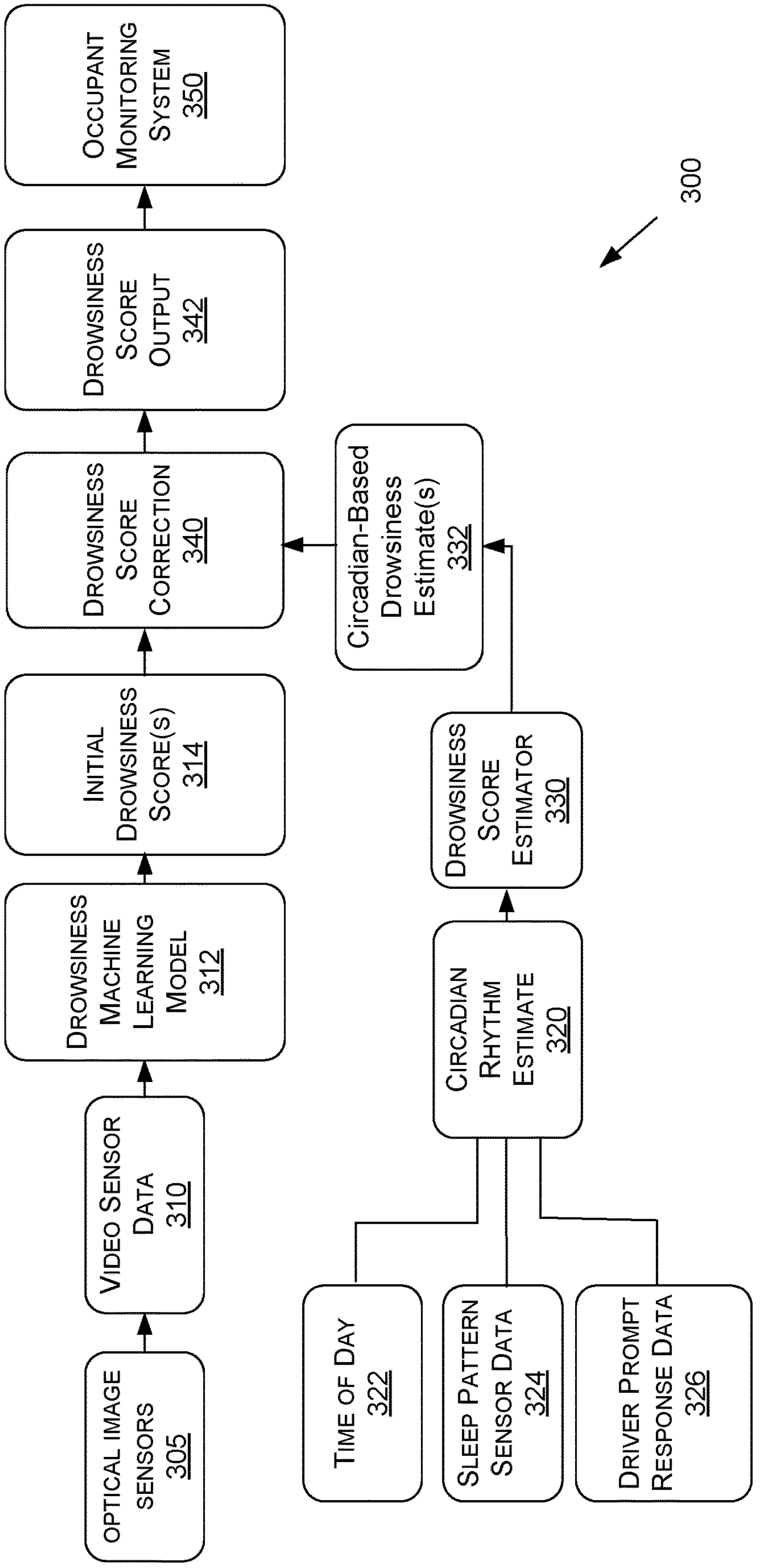
FIG. 3 is a data flow diagram for a circadian rhythm-based drowsiness detection system, in accordance with some embodiments of the present disclosure.
Figure 4:
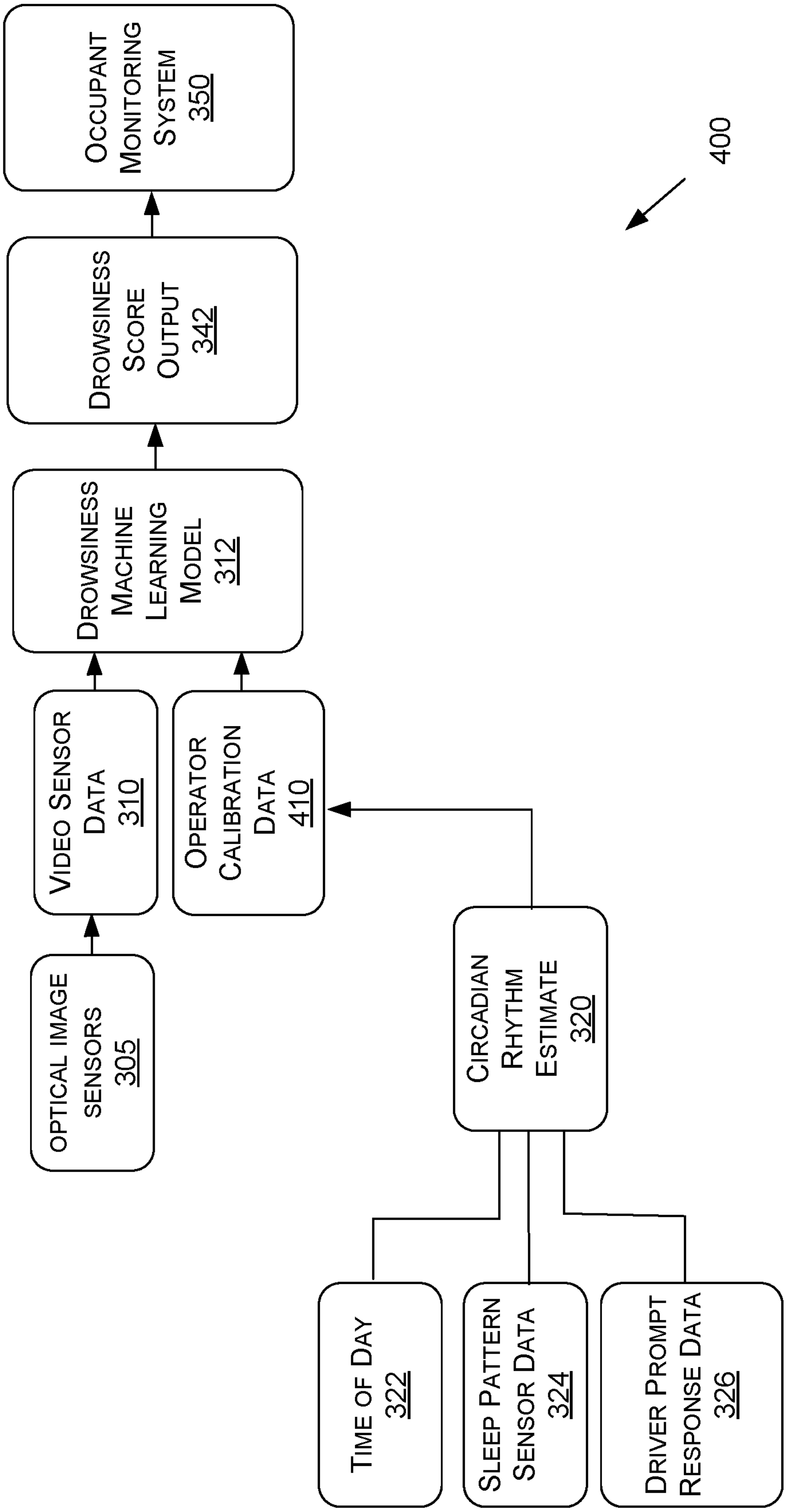
FIG. 4 is a data flow diagram for a circadian rhythm-based drowsiness detection system using occupant calibration data, in accordance with some embodiments of the present disclosure.
Figure 5:
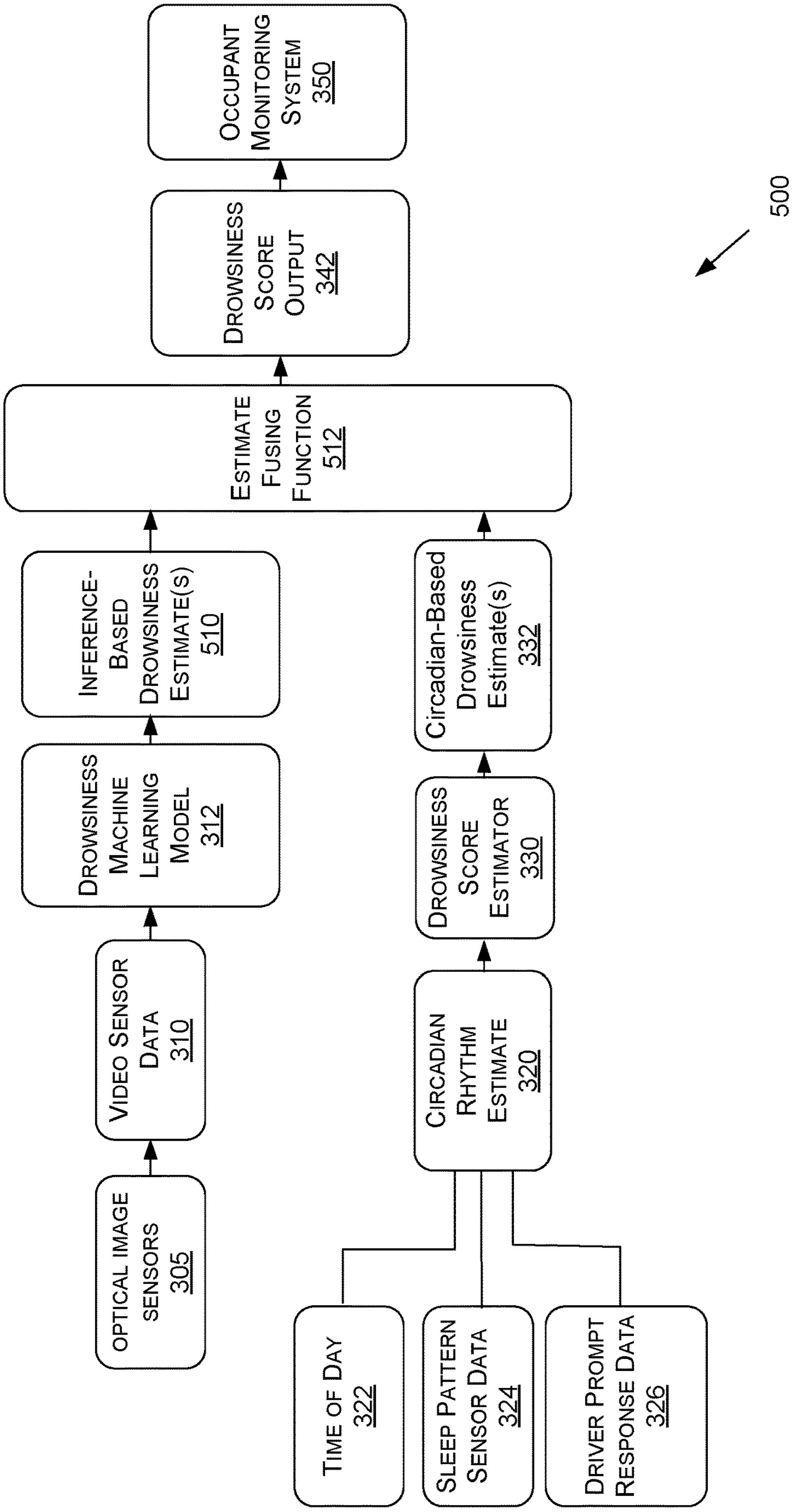
FIG. 5 is a data flow diagram for a circadian rhythm-based drowsiness detection system using estimate fusing, in accordance with some embodiments of the present disclosure.

With reference now to FIGS. 3-5, these figures illustrate example data flow diagrams for different embodiments of a circadian rhythm-based drowsiness detection system, in accordance with the present disclosure. It should be understood that this and other arrangements described herein are set forth only as examples. Other arrangements and elements (e.g., machines, interfaces, functions, orders, groupings of functions, etc.) may be used in addition to or instead of those shown, and some elements may be omitted altogether. Further, many of the elements described herein are functional entities that may be implemented as discrete or distributed components or in conjunction with other components, and in any suitable combination and location. Various functions described herein as being performed by entities may be carried out by hardware, firmware, and/or software. For instance, various functions may be carried out by a processor executing instructions stored in memory. In some embodiments, the systems, methods, and processes described herein may be executed using similar components, features, and/or functionalities to those of example autonomous vehicle 800 of FIGS. 8A-8D, example computing device 900 of FIG. 9, and/or example data center 1000 of FIG. 10. For example, in some embodiments, the circadian rhythm-based drowsiness detection systems illustrated in FIGS. 3-4 may generate a drowsiness score output for input into an occupant monitoring system (OMS) as described with respect to the example autonomous vehicle 800 of FIGS. 8A-8D.

With reference to FIG. 3, FIG. 3 is an example data flow diagram for a circadian rhythm-based drowsiness detection system 300, in accordance with the present disclosure. Circadian rhythm-based drowsiness detection system 300 uses video sensor data 310 that captures video images of a vehicle occupant (e.g., the vehicle driver or operator of vehicle 800) and produces a drowsiness score output 342 that can be used by other systems to control operations of the vehicle 800, such as an occupant monitoring system 350. The resulting drowsiness score output 342 may represent drowsiness using a standardized drowsiness score scale, such as KSS drowsiness score values. In some embodiments, based at least in part on the drowsiness score output 342, OMS 350 may perform real-time assessments of driver and occupant presence, gaze, alertness, or other conditions for reliable detection and recognition of safety-critical information.

Based on the drowsiness score output 342, the OMS 350 may trigger one or more safety operations, such as audio and/or visual warnings that may be used to stimulate the driver's alertness, advise the driver to pull over and stop the vehicle, and/or alert other occupants in the vehicle of the driver's drowsiness. In some embodiments, automated actions reported by the OMS 350 in response to driver drowsiness may be tiered based on the driver's level of drowsiness indicated by the drowsiness score output 342. In some embodiments, the real-time drowsiness detection system may also operate using a tiered system where the drowsiness score output 342 is generated less frequently when drowsiness scores are in a first range where the driver appears less drowsy, and more frequently when drowsiness scores are in a second range where the driver appears more drowsy.

Video sensor data 310 may represent video frames captured by one or more optical image sensors 305, such as the one or more occupant monitoring system (OMS) sensor(s) 801 described with respect to FIG. 8. Optical image sensors 305 may include camera or other optical sensor that captures, as non-limiting examples, RGB, IR, and/or RGB-IR image frames. The circadian rhythm-based drowsiness detection system 300 may include a drowsiness machine learning model 312 trained to infer a vehicle occupant's drowsiness based on the video sensor data 310. For example, the drowsiness machine learning model 312 may comprise a machine learning model such as the drowsiness machine learning model 170 that is trained using ground truth training data that comprises samples of video sequences of test subjects labeled to indicate an estimated drowsiness of the test subject. In some embodiments, the drowsiness machine learning model 312 may be trained using corrected GT training data 160 produced as described with respect to the circadian rhythm-based ground truth correction system 100 of FIG. 1. Based on the inferred vehicle occupant's drowsiness, the drowsiness machine learning model 312 may output an initial drowsiness score 314 that represents a prediction of the drowsiness of the vehicle occupant.

As shown in FIG. 3, in some embodiments, a circadian-based drowsiness estimate 332 may be used to correct the initial drowsiness score 314 predicted by the drowsiness machine learning model 312. Similar to the case of the test subjects discussed above, for a circadian rhythm-based drowsiness detection system 300, a driver of vehicle 800 may experience a level of drowsiness over the course of a drive that varies depending on where the driver is with respect to their circadian rhythm. However, such changes in driver drowsiness due to the cycle of the circadian rhythm is expected to vary gradually over time. Accordingly, the initial drowsiness score 314 predicted by the drowsiness machine learning model 312 can be expected to gradually change over time over the course of a drive, but are not expected to change substantially from one prediction to the next. In the embodiment of FIG. 3, a circadian-based drowsiness estimate 332 may be computed to estimate a position of the vehicle driver with respect to their circadian rhythm process C curve (such as is discussed with respect to the process C curve of FIG. 2). Using a circadian rhythm estimate 320 for the driver, an alertness level for the driver may be estimated based on an input representing the time of day 322, locating the position in the circadian rhythm cycle associated with that time of day 322 on the C-curve of the circadian rhythm estimate 320 for the driver, and determining the corresponding circadian-based alertness level from the value of the C-curve at that position. The circadian-based alertness level may be converted to a drowsiness score by drowsiness score estimator 330 to generate the circadian-based drowsiness estimate 332 used to correct the initial drowsiness score 314.

In some embodiments, the driver's position on the process C curve for circadian rhythm estimate 320 may be refined based on additional information about the timing and/or quality of the driver's recent sleep. For example, in some embodiments, the driver may wear a sensor (e.g., on a wearable device) that records sleep data from the driver's prior sleep period to produce sleep pattern sensor data 324. Sleep pattern sensor data 324 may include quantified metrics that characterize the quality of the driver's last sleep and/or the time they awoke. In some embodiments the circadian rhythm estimate 320 may be adjusted or calibrated with respect to its time-of-day scale by an offset computed based on sleep quality or time they awoke. For example, if the driver normally wakes up earlier than the defined nominal wake-up time for a process C curve (e.g., they normally wake at 4:00 am rather than 7:00 am), then the process C curve for the circadian rhythm estimate 320 may be offset based on that 3-hour difference to calibrate it to the normal wake-up time of that driver. As another example, if the time of day 322 indicates that it is 11:00 am but the sleep pattern sensor data 324 indicates that the driver woke up from their last sleep period eight hours ago, the circadian rhythm estimate 320 may be adjusted to position the subject further down the process C curve based on the difference between the defined nominal wake-up time and the time the driver actually awoke.

In some embodiments, circadian rhythm estimate 320 may be adjusted or calibrated with respect to its time-of-day scale by an offset computed based on driver prompt response data 326. For example, when the driver enters vehicle 800, they may be asked what time they last woke up from sleep, asked about the quality of their sleep, and/or if they've consumed any stimulants (e.g., coffee). Based on such driver prompt response data 326, the driver's initial position on the process C curve can be more accurately established from the circadian rhythm estimate 320 to obtain a more accurate and corresponding expected driver alertness level from the process C curve. The alertness level established from the circadian rhythm estimate 320 may be used by the drowsiness score estimator 330 to convert the alertness level from the circadian rhythm estimate 320 to the circadian-based drowsiness estimate 332 used to correct the initial drowsiness score 314.

In some embodiments, while the driver is operating the vehicle, the drowsiness score estimator 330 may compute and weigh into the circadian-based drowsiness estimate 320 a time-on-task factor that further accounts for fatigue resulting from the time the driver has been operating the vehicle.

In the embodiment shown in FIG. 3, the circadian rhythm-based drowsiness detection system 300 includes a drowsiness score correction function 340 that monitors the initial drowsiness score 314 and determines when the initial drowsiness score 314 appears potentially inaccurate. For example, for each drowsiness score prediction inferred by the drowsiness machine learning model 312, the drowsiness machine learning model 312 may also output a confidence value indicating its confidence that the drowsiness score prediction is an accurate prediction. For example, an initial drowsiness score 314 generated from video sensor data 310 where the driver's face is partially blocked (e.g., by the driver's hand), the drowsiness machine learning model 312 may infer a drowsiness score prediction, but that prediction may include a confidence value that is lower than it would be if the video sensor data 310 instead provided an unobstructed view of the driver's face. In other embodiments, the drowsiness score correction function 340 may determine that a drowsiness score prediction represents an unexpected step-change in driver drowsiness compared to a prior drowsiness score prediction and/or otherwise inconsistent with recent trending of drowsiness score prediction (e.g., greater than a threshold). When the drowsiness score correction function 340 determines that one or more drowsiness score predictions from the initial drowsiness score 314 are potentially inaccurate, the drowsiness score correction function 340 may use the circadian-based drowsiness estimate 332 to compute a correction to the initial drowsiness score 314. The drowsiness score output 342 may then represent the corrected drowsiness score computed by the drowsiness score correction function 340.

In some embodiments, to compute the corrected drowsiness score, the circadian-based drowsiness estimate 332 may be combined with initial drowsiness score 314 inferred by drowsiness machine learning model 312, for example, using a weighted sum. In some embodiments, the weighting of the weighted sum may be based on a prediction confidence value, where the lower the confidence value for the initial drowsiness score 314, the higher the weighting given to the circadian-based drowsiness estimate 332. In some embodiments, the drowsiness score correction function 340 may replace one or more drowsiness score predictions inferred by drowsiness machine learning model 312 using the circadian-based drowsiness estimate 332.

With reference now to FIG. 4, FIG. 4 is an example data flow diagram for a circadian rhythm-based drowsiness detection system 400 where the circadian rhythm estimate 320 may be used to generate occupant (e.g., operator) calibration data 410 to calibrate inputs to the drowsiness machine learning model 312 so that the model more accurately generates drowsiness score predictions for the drowsiness score output 342. For example, each vehicle driver may have personal observable physiological patterns that correspond with their level of drowsiness. In some embodiments, a circadian rhythm process C curve of the circadian rhythm estimate 320 may be calibrated to an individual driver, and a circadian rhythm-based drowsiness estimate baseline established for the driver established to produce the operator calibration data 410. The operator calibration data 410 may be associated with an observable indicia of drowsiness derived from the video sensor data 310 so that the drowsiness machine learning model 312 can further incorporate personal driver calibration data to produce more accurate inferred drowsiness score predictions based on the video sensor data 310. For example, a driver may have a particular blinking patterns (other indicia of drowsiness) that changes with their level of drowsiness (e.g., how they blink regularly when they are alert versus drowsy). When this driver assumes operation of a vehicle, their initial position on the process C curve for the circadian rhythm estimate 320 can be estimated as described above (e.g., based on time of day, sensor data, response to prompts, and the like). Based on that initial position on the process C curve, a corresponding expected drowsiness level may be derived and associated with the driver's current blinking pattern behavior to produce operator calibration data 410. The operator calibration data 410 for that driver may be stored into memory as a personal calibration parameter that may be recalled for use in the future, for example, as an input to the drowsiness machine learning model 312. The operator calibration data 410 may include one or more offsets, biases, or other operator calibration data that the drowsiness machine learning model 312 may use to shift its drowsiness score predictions when that driver is operating the vehicle. In some embodiments, operator calibration data 410 associated with a driver may be maintained as valid for a prescribed period of time (e.g., 8 hours, 24 hours, the length of a driving session allowing for breaks of limited duration) and recomputed once the prescribed period of time has expired.

With reference now to FIG. 5, FIG. 5 is an example data flow diagram for a circadian rhythm-based drowsiness detection system 500 where the circadian rhythm estimate 320 may be used as a parallel assessment of driver drowsiness used together with the inferred drowsiness score predictions from the drowsiness machine learning model 312 to compute the drowsiness score output 342. In these embodiments, circadian-based drowsiness estimate(s) 332 may be computed based on a circadian rhythm estimate 320, such as described with respect to FIG. 3. The drowsiness machine learning model 312 may produce drowsiness score predictions from video sensor data 310, such as is described with respect to FIG. 3, which are referred to in FIG. 5 as inference-based drowsiness estimate(s) 510. Here, the estimate fusing function 512 computes the drowsiness score output 342 using the combination of the circadian-based drowsiness estimate(s) 332 and the inference-based drowsiness estimate(s) 510. For example, the estimate fusing function 512 may average circadian-based drowsiness estimate(s) 332 and the inference-based drowsiness estimate(s) 510 or otherwise statistically combine the estimates to compute the drowsiness score output 342.

Now referring to FIG. 6, FIG. 6 is a flow diagram showing a method 600 for circadian rhythm-based ground truth correction, in accordance with some embodiments of the present disclosure. It should be understood that the features and elements described herein with respect to the method 600 of FIG. 6 may be used in conjunction with, in combination with, or substituted for elements of any of the other embodiments discussed herein and vice versa. Further, it should be understood that the functions, structures, and other descriptions of elements for embodiments described in FIG. 6 may apply to like or similarly named or described elements across any of the figures and/or embodiments described herein and vice versa.

Each block of method 600, described herein, comprises a computing process that may be performed using any combination of hardware, firmware, and/or software. For instance, various functions may be carried out by a processor executing instructions stored in memory. The methods may also be embodied as computer-usable instructions stored on computer storage media. The methods may be provided by a standalone application, a service or hosted service (standalone or in combination with another hosted service), or a plugin to another product, to name a few. In addition, method 600 is described, by way of example, with respect to the circadian rhythm-based ground truth correction system 100 of FIG. 1. However, these methods may additionally or alternatively be executed by any one system, or any combination of systems, including, but not limited to, those described herein.

As discussed herein in greater detail, the method may include generating a second ground truth image sequence from a first ground truth image sequence by applying one or more drowsiness corrections to one or more labels of the first ground truth image sequence, the one or more drowsiness corrections determined using a drowsiness score estimate for a test subject during a testing period associated with the first ground truth image sequence, the drowsiness score estimate based at least on correlating a circadian rhythm process to the test subject at a time of the testing period.

The method 600, at block B602, includes receiving a first ground truth image sequence representing visual characteristics of a test subject in the first ground truth image sequence during a testing period, the first ground truth image sequence comprising one or more drowsiness labels indicating a drowsiness of the test subject. The first ground truth image sequence may capture visual characteristics of the test subject performing one or more psychomotor vigilance tests (PVTs) over a course of the testing period. Visual characteristics of the test subject in the first ground truth image sequence may comprise at least one of an eye blink rate, an eye blink velocity, an eye blink amplitude, a time of eye closure, a head pose, an eye gaze direction, a pattern of yawning behavior, and/or other characteristics indicative of drowsiness.

The method 600, at block B604, includes correlating a position on a circadian rhythm process to a time of the testing period. The circadian rhythm process may correspond to a circadian rhythm process C curve. For example, as described with respect to FIG. 2, an alertness level estimate may be obtained from a process C curve by correlating a time of day to a value of the process C curve for that time of day. In some embodiments, an alertness value may be determined that corresponds to the position on the circadian rhythm process based at least on a time of day and sensor data representing sleep information measured from the test subject. In some embodiments, an alertness value may be determined that corresponds to the position on the circadian rhythm process based at least on a time of day and sleep information based at least on responses to questions to the test subject.

The method 600, at block B606, includes applying one or more drowsiness corrections to the one or more drowsiness labels based at least on an alertness value corresponding to the position on the circadian rhythm process to generate a second ground truth image sequence. In some embodiments, the one or more drowsiness corrections may be computed based at least on the alertness value corresponding to the position on the circadian rhythm process and time-on-task data associated with a task performed by the test subject during the testing period. In one or more embodiments, the one or more drowsiness corrections may be based at least on the alertness value corresponding to the position on the circadian rhythm process and one or more alertness test measurements captured from the test subject during the testing period. Examples of such test measurements include, but are not limited to, measurements from an electroencephalogram (EEG) test and/or a mean reaction time (MRT) test and/or observer rated drowsiness (ORD). One or more drowsiness labels of the second ground truth image sequence may comprise a score, for example, based at least on a Karolinska Sleepiness Scale (KSS).

The method 600, at block B608, includes training a machine learning model to infer a drowsiness level based on the second ground truth image sequence. As discussed with respect to FIG. 1, the corrected ground truth training data 160 may be used in processes to train a machine learning model to detect drowsiness. Such a machine learning model may include a drowsiness detection deep neural network (DNN). The machine learning model may input corrected ground truth training data and infer the test subject's drowsiness based on features observable from an image sequence such as blink rate, blink velocity, blink amplitude, time of eye closure, head pose (e.g., upright versus slouched), eye gaze patterns (e.g., where the subject's eyes are gazing), yawning patterns, and/or other observable parameters that evidence drowsiness. The drowsiness machine learning model may generate drowsiness level predictions, for example, that represent drowsiness of the test subject using the KSS. Drowsiness level predictions inferred during training of the machine learning model may be compared to the corrected drowsiness labels of the corrected ground truth training data to generate a loss feedback for adjusting the machine learning model to improve the accuracy of its drowsiness level predictions.

Figure 7:
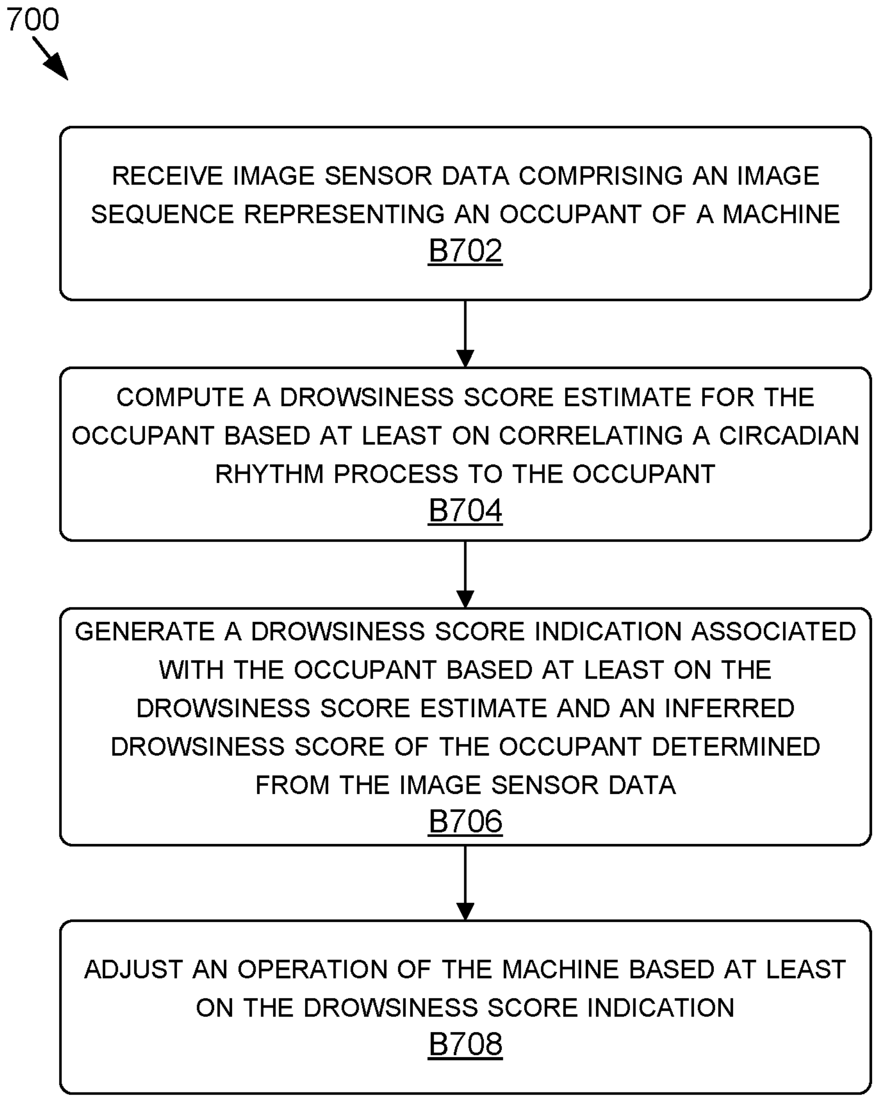
FIG. 7 is a flow diagram for a method for a circadian rhythm-based drowsiness detection system, in accordance with some embodiments of the present disclosure.

Now referring to FIG. 7, FIG. 7 is a flow diagram showing a method 700 for circadian rhythm-based drowsiness detection, in accordance with some embodiments of the present disclosure. It should be understood that the features and elements described herein with respect to the method 700 of FIG. 7 may be used in conjunction with, in combination with, or substituted for elements of any of the other embodiments discussed herein and vice versa. Further, it should be understood that the functions, structures, and other descriptions of elements for embodiments described in FIG. 7 may apply to like or similarly named or described elements across any of the figures and/or embodiments described herein and vice versa.

Each block of method 700, described herein, comprises a computing process that may be performed using any combination of hardware, firmware, and/or software. For instance, various functions may be carried out by a processor executing instructions stored in memory. The methods may also be embodied as computer-usable instructions stored on computer storage media. The methods may be provided by a standalone application, a service or hosted service (standalone or in combination with another hosted service), or a plugin to another product, to name a few. In addition, method 700 is described, by way of example, with respect to the circadian rhythm-based drowsiness detection systems described with respect to FIGS. 3-5. However, these methods may additionally or alternatively be executed by any one system, or any combination of systems, including, but not limited to, those described herein.

As discussed herein in greater detail, the method may include generating a drowsiness score indication associated with an operator of a machine based at least on a drowsiness score estimate determined from a position on a circadian rhythm process and a drowsiness score inferred from image sensor data comprising an image sequence of the operator.

The method 700, at block B702, includes receiving image sensor data comprising an image sequence representing an occupant (e.g., a driver, operator, and/or other occupant) of a machine. The machine may include an automobile such as vehicle 800 and/or a passenger vehicle, such as a car, a truck, a bus, a first responder vehicle, a shuttle, an electric or motorized bicycle, a motorcycle, a fire truck, a police vehicle, an ambulance, a boat, a construction vehicle, an underwater craft, a robotic vehicle, a drone, an airplane, a vehicle coupled to a trailer (e.g., a semi-tractor-trailer truck used for hauling cargo), and/or another type of vehicle (e.g., that is unmanned and/or that accommodates one or more passengers). The image sensor data may represent visual characteristics of the occupant such as at least one of an eye blink rate, an eye blink velocity, an eye blink amplitude, a time of eye closure, a head pose, an eye gaze direction, a pattern of yawning behavior, and/or other characteristics indicative of drowsiness.

The method 700, at block B704, includes computing a drowsiness score estimate for the occupant based at least on correlating a circadian rhythm process to the occupant. The circadian rhythm process may correspond to a circadian rhythm process C curve. For example, as described with respect to FIG. 2, an alertness level estimate may be obtained from a process C curve by correlating a time of day to a value of the process C curve for that time of day. In some embodiments, an alertness value may be determined that corresponds to the position on the circadian rhythm process based at least on a time of day and sensor data representing sleep information measured from the occupant. In some embodiments, an alertness value may be determined that corresponds to the position on the circadian rhythm process based at least on a time of day and sleep information based at least on responses to questions to the occupant.

The method 700, at block B706, includes generating a drowsiness score indication associated with the occupant based at least on the drowsiness score estimate and an inferred drowsiness score of the occupant determined from the image sensor data. The inferred drowsiness score may comprise a drowsiness level prediction inferred by a machine learning model (such as drowsiness machine learning model 312), and/or include a drowsiness detection deep neural network (DNN). The inferred drowsiness score may be predicted by a machine learning model based at least on the image sensor data and at least one personal calibration parameter derived from the circadian rhythm process, such as described with respect to FIG. 4. For example, a personal calibration parameter may be recalled from a memory based at least on determining an identity associated with the occupant. The drowsiness score estimate may be determined based at least on an alertness value corresponding to a position on the circadian rhythm process, the position determined based at least on a time of day. In some embodiments, the drowsiness score estimate can be determined based at least on an alertness value corresponding to a position on the circadian rhythm process, the position determined based at least on a time of day and sensor data representing sleep information measured from the occupant. In some embodiments, the drowsiness score estimate may be determined based at least on an alertness value corresponding to a position on the circadian rhythm process, the position determined based at least on a time of day and sleep information based at least on responses to questions to the occupant. One or more drowsiness corrections may be computed and applied to the inferred drowsiness score based at least on an alertness value corresponding to a position on the circadian rhythm process and time-on-task data associated with the occupant operating the machine. The inferred drowsiness score of the occupant from the image sensor data may be predicted based at least on at least one of: an eye blink rate, an eye blink velocity, an eye blink amplitude, a time of eye closure, a head pose, an eye gaze direction, and/or a pattern of yawning behavior, for example. The drowsiness score indication may be computed based at least on combining the inferred drowsiness score with the drowsiness score estimate using a smoothing algorithm. In some embodiments, the drowsiness score estimate may be output as the drowsiness score indication based at least on determining that the inferred drowsiness score is anomalous and/or is has a low-confidence score. In some embodiments, the drowsiness score indication may comprise a score, for example, based at least on a Karolinska Sleepiness Scale (KSS).

The method 700, at block B708, includes adjusting an operation of the machine based at least on the drowsiness score indication. The drowsiness score indication may include a drowsiness score output that can be used by other systems to control operations of the vehicle 800, such as an occupant monitoring system (OMS). Based at least in part on the drowsiness score indication, an OMS may perform real-time assessments of driver and occupant presence, gaze, alertness, or other conditions for reliable detection and recognition of safety-critical information. Based on the drowsiness score indication, an OMS may trigger one or more safety operations, such as audio and/or visual warnings that may be used to stimulate the driver's alertness, advise the driver to pull over and stop the vehicle, and/or alert other occupants in the vehicle of the driver's drowsiness, such as described herein.

The systems and methods described herein may be used by, without limitation, non-autonomous vehicles, semi-autonomous vehicles (e.g., in one or more adaptive driver assistance systems (ADAS)), piloted and un-piloted robots or robotic platforms, warehouse vehicles, off-road vehicles, vehicles coupled to one or more trailers, flying vessels, boats, shuttles, emergency response vehicles, motorcycles, electric or motorized bicycles, aircraft, construction vehicles, trains, underwater craft, remotely operated vehicles such as drones, and/or other vehicle types. Further, the systems and methods described herein may be used for a variety of purposes, by way of example and without limitation, for machine control, machine locomotion, machine driving, synthetic data generation, model training, perception, augmented reality, virtual reality, mixed reality, robotics, security and surveillance, simulation and digital twinning, autonomous or semi-autonomous machine applications, deep learning, environment simulation, object or actor simulation and/or digital twinning, data center processing, conversational AI, light transport simulation (e.g., ray-tracing, path tracing, etc.), collaborative content creation for 3D assets, cloud computing, generative AI, and/or any other suitable applications.

Disclosed embodiments may be comprised in a variety of different systems such as automotive systems (e.g., a control system for an autonomous or semi-autonomous machine, a perception system for an autonomous or semi-autonomous machine), systems implemented using a robot, aerial systems, medial systems, boating systems, smart area monitoring systems, systems for performing deep learning operations, systems for performing simulation operations, systems for performing digital twin operations, systems implemented using an edge device, systems incorporating one or more virtual machines (VMs), systems for performing synthetic data generation operations, systems implemented at least partially in a data center, systems for performing conversational AI operations, systems implementing one or more language models-such as one or more large language models (LLMs), systems for performing light transport simulation, systems for performing collaborative content creation for 3D assets, systems implemented at least partially using cloud computing resources, and/or other types of systems.

Example Autonomous Vehicle

Figure 8A:
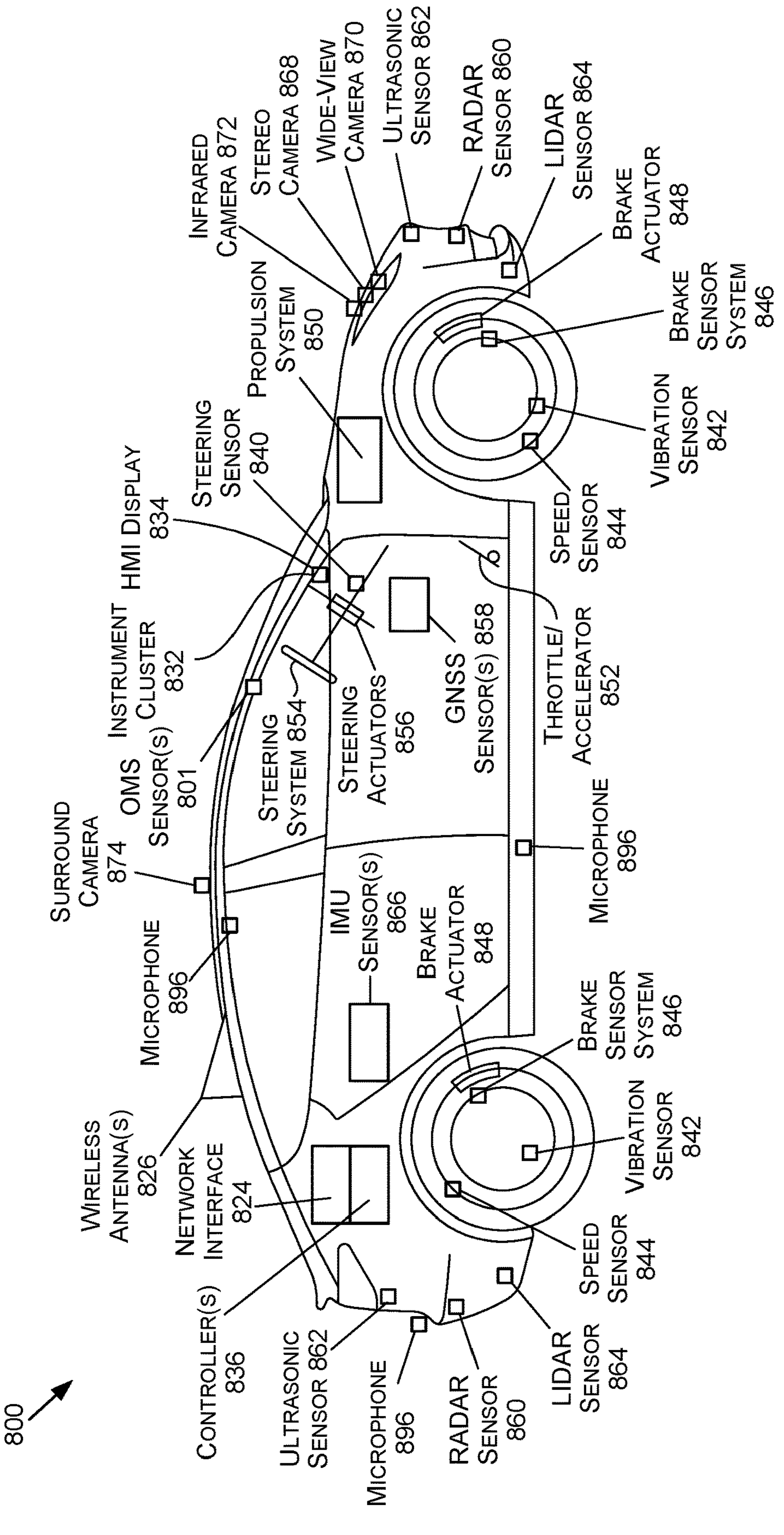
FIG. 8A is an illustration of an example autonomous vehicle, in accordance with some embodiments of the present disclosure.

FIG. 8A is an illustration of an example autonomous vehicle 800, in accordance with some embodiments of the present disclosure. The autonomous vehicle 800 (alternatively referred to herein as the "vehicle 800") may include, without limitation, a passenger vehicle, such as a car, a truck, a bus, a first responder vehicle, a shuttle, an electric or motorized bicycle, a motorcycle, a fire truck, a police vehicle, an ambulance, a boat, a construction vehicle, an underwater craft, a robotic vehicle, a drone, an airplane, a vehicle coupled to a trailer (e.g., a semi-tractor-trailer truck used for hauling cargo), and/or another type of vehicle (e.g., that is unmanned and/or that accommodates one or more passengers). Autonomous vehicles are generally described in terms of automation levels, defined by the National Highway Traffic Safety Administration (NHTSA), a division of the US Department of Transportation, and the Society of Automotive Engineers (SAE) "Taxonomy and Definitions for Terms Related to Driving Automation Systems for On-Road Motor Vehicles" (Standard No. J3016-201806, published on Jun. 15, 2018, Standard No. J3016-201609, published on Sep. 30, 2016, and previous and future versions of this standard). The vehicle 800 may be capable of functionality in accordance with one or more of Level 3-Level 5 of the autonomous driving levels. The vehicle 800 may be capable of functionality in accordance with one or more of Level 1-Level 5 of the autonomous driving levels. For example, the vehicle 800 may be capable of driver assistance (Level 1), partial automation (Level 2), conditional automation (Level 3), high automation (Level 4), and/or full automation (Level 5), depending on the embodiment. The term "autonomous," as used herein, may include any and/or all types of autonomy for the vehicle 800 or other machine, such as being fully autonomous, being highly autonomous, being conditionally autonomous, being partially autonomous, providing assistive autonomy, being semi-autonomous, being primarily autonomous, or other designation.

The vehicle 800 may include components such as a chassis, a vehicle body, wheels (e.g., 2, 4, 6, 8, 18, etc.), tires, axles, and other components of a vehicle. The vehicle 800 may include a propulsion system 850, such as an internal combustion engine, hybrid electric power plant, an all-electric engine, and/or another propulsion system type. The propulsion system 850 may be connected to a drive train of the vehicle 800, which may include a transmission, to enable the propulsion of the vehicle 800. The propulsion system 850 may be controlled in response to receiving signals from the throttle/accelerator 852.

A steering system 854, which may include a steering wheel, may be used to steer the vehicle 800 (e.g., along a desired path or route) when the propulsion system 850 is operating (e.g., when the vehicle is in motion). The steering system 854 may receive signals from a steering actuator 856. The steering wheel may be optional for full automation (Level 5) functionality.

The brake sensor system 846 may be used to operate the vehicle brakes in response to receiving signals from the brake actuators 848 and/or brake sensors.

Controller(s) 836, which may include one or more system on chips (SoCs) 804 (FIG. 8C) and/or GPU(s), may provide signals (e.g., representative of commands) to one or more components and/or systems of the vehicle 800. For example, the controller(s) may send signals to operate the vehicle brakes via one or more brake actuators 848, to operate the steering system 854 via one or more steering actuators 856, to operate the propulsion system 850 via one or more throttle/accelerators 852. The controller(s) 836 may include one or more onboard (e.g., integrated) computing devices (e.g., supercomputers) that process sensor signals, and output operation commands (e.g., signals representing commands) to enable autonomous driving and/or to assist a human driver in driving the vehicle 800. The controller(s) 836 may include a first controller 836 for autonomous driving functions, a second controller 836 for functional safety functions, a third controller 836 for artificial intelligence functionality (e.g., computer vision), a fourth controller 836 for infotainment functionality, a fifth controller 836 for redundancy in emergency conditions, and/or other controllers. In some examples, a single controller 836 may handle two or more of the above functionalities, two or more controllers 836 may handle a single functionality, and/or any combination thereof. In some embodiments, one or more aspects and/or functions described with respect to any of the circadian rhythm-based drowsiness detection systems described herein may be implemented at least in part by controllers 836.

The controller(s) 836 may provide the signals for controlling one or more components and/or systems of the vehicle 800 in response to sensor data received from one or more sensors (e.g., sensor inputs). The sensor data may be received from, for example and without limitation, global navigation satellite systems ("GNSS") sensor(s) 858 (e.g., Global Positioning System sensor(s)), RADAR sensor(s) 860, ultrasonic sensor(s) 862, LIDAR sensor(s) 864, inertial measurement unit (IMU) sensor(s) 866 (e.g., accelerometer(s), gyroscope(s), magnetic compass(es), magnetometer(s), etc.), microphone(s) 896, stereo camera(s) 868, wide-view camera(s) 870 (e.g., fisheye cameras), infrared camera(s) 872, surround camera(s) 874 (e.g., 360 degree cameras), long-range and/or mid-range camera(s) 898, speed sensor(s) 844 (e.g., for measuring the speed of the vehicle 800), vibration sensor(s) 842, steering sensor(s) 840, brake sensor(s) (e.g., as part of the brake sensor system 846), one or more occupant monitoring system (OMS) sensor(s) 801 (e.g., one or more interior cameras), and/or other sensor types.

One or more of the controller(s) 836 may receive inputs (e.g., represented by input data) from an instrument cluster 832 of the vehicle 800 and provide outputs (e.g., represented by output data, display data, etc.) via a human-machine interface (HMI) display 834, an audible annunciator, a loudspeaker, and/or via other components of the vehicle 800. The outputs may include information such as vehicle velocity, speed, time, map data (e.g., the High Definition ("HD") map 822 of FIG. 8C), location data (e.g., the vehicle's 800 location, such as on a map), direction, location of other vehicles (e.g., an occupancy grid), information about objects and status of objects as perceived by the controller(s) 836, etc. For example, the HMI display 834 may display information about the presence of one or more objects (e.g., a street sign, caution sign, traffic light changing, etc.), and/or information about driving maneuvers the vehicle has made, is making, or will make (e.g., changing lanes now, taking exit 34B in two miles, etc.).

The vehicle 800 further includes a network interface 824 which may use one or more wireless antenna(s) 826 and/or modem(s) to communicate over one or more networks. For example, the network interface 824 may be capable of communication over Long-Term Evolution ("LTE"), Wide-band Code Division Multiple Access ("WCDMA"), Universal Mobile Telecommunications System ("UMTS"), Global System for Mobile communication ("GSM"), IMT-CDMA Multi-Carrier ("CDMA2000"), etc. The wireless antenna(s) 826 may also enable communication between objects in the environment (e.g., vehicles, mobile devices, etc.), using local area network(s), such as Bluetooth, Bluetooth Low Energy ("LE"), Z-Wave, ZigBee, etc., and/or low power wide-area network(s) ("LPWANs"), such as LoRaWAN, SigFox, etc.

Figure 8B:
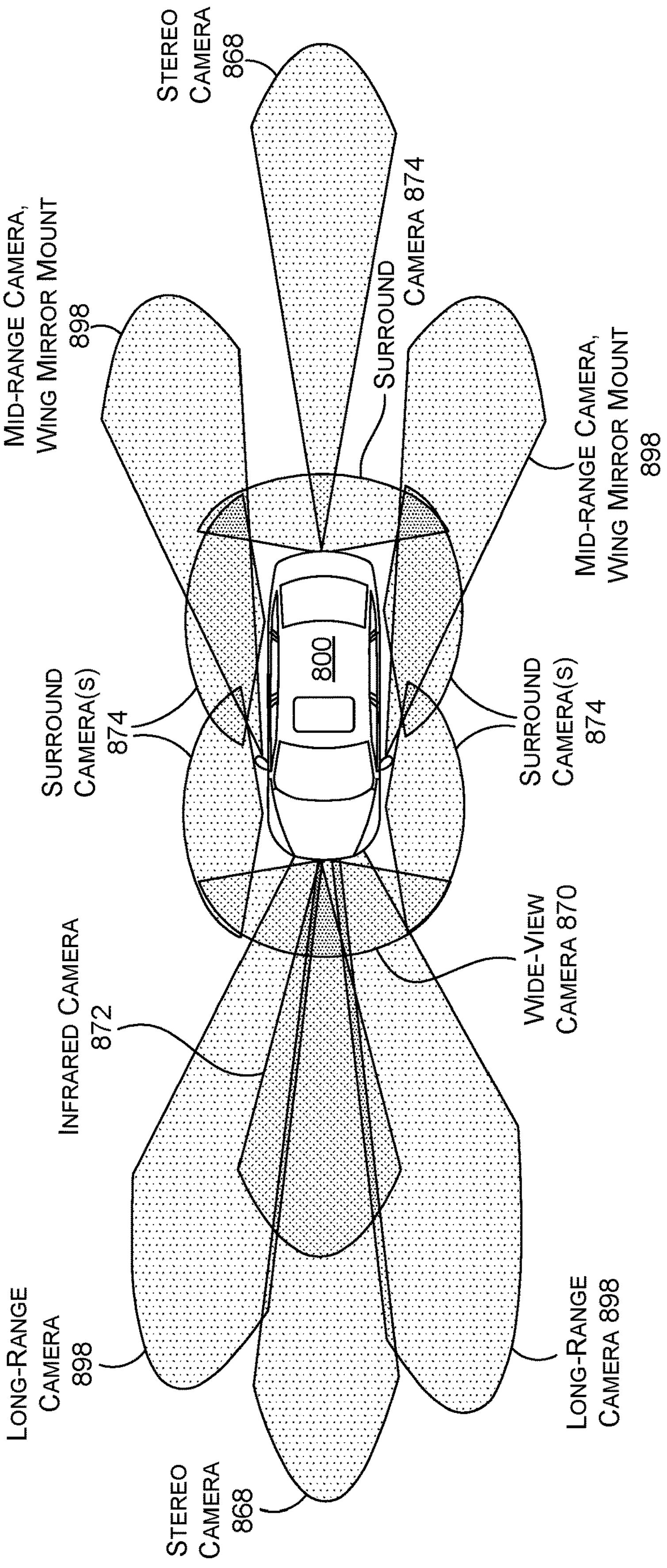
FIG. 8B is an example of camera locations and fields of view for the example autonomous vehicle of FIG. 8A, in accordance with some embodiments of the present disclosure.

FIG. 8B is an example of camera locations and fields of view for the example autonomous vehicle 800 of FIG. 8A, in accordance with some embodiments of the present disclosure. The cameras and respective fields of view are one example embodiment and are not intended to be limiting. For example, additional and/or alternative cameras may be included and/or the cameras may be located at different locations on the vehicle 800.

The camera types for the cameras may include, but are not limited to, digital cameras that may be adapted for use with the components and/or systems of the vehicle 800. The camera(s) may operate at automotive safety integrity level (ASIL) B and/or at another ASIL. The camera types may be capable of any image capture rate, such as 60 frames per second (fps), 120 fps, 240 fps, etc., depending on the embodiment. The cameras may be capable of using rolling shutters, global shutters, another type of shutter, or a combination thereof. In some examples, the color filter array may include a red clear clear clear (RCCC) color filter array, a red clear clear blue (RCCB) color filter array, a red blue green clear (RBGC) color filter array, a Foveon X3 color filter array, a Bayer sensors (RGGB) color filter array, a monochrome sensor color filter array, and/or another type of color filter array. In some embodiments, clear pixel cameras, such as cameras with an RCCC, an RCCB, and/or an RBGC color filter array, may be used in an effort to increase light sensitivity.

In some examples, one or more of the camera(s) may be used to perform advanced driver assistance systems (ADAS) functions (e.g., as part of a redundant or fail-safe design). For example, a Multi-Function Mono Camera may be installed to provide functions including lane departure warning, traffic sign assist and intelligent headlamp control. One or more of the camera(s) (e.g., all of the cameras) may record and provide image data (e.g., video) simultaneously.

One or more of the cameras may be mounted in a mounting assembly, such as a custom designed (three dimensional ("3D") printed) assembly, in order to cut out stray light and reflections from within the car (e.g., reflections from the dashboard reflected in the windshield mirrors) which may interfere with the camera's image data capture abilities. With reference to wing-mirror mounting assemblies, the wing-mirror assemblies may be custom 3D printed so that the camera mounting plate matches the shape of the wing-mirror. In some examples, the camera(s) may be integrated into the wing-mirror. For side-view cameras, the camera(s) may also be integrated within the four pillars at each corner of the cabin.

Cameras with a field of view that include portions of the environment in front of the vehicle 800 (e.g., front-facing cameras) may be used for surround view, to help identify forward facing paths and obstacles, as well aid in, with the help of one or more controllers 836 and/or control SoCs, providing information critical to generating an occupancy grid and/or determining the preferred vehicle paths. Front-facing cameras may be used to perform many of the same ADAS functions as LIDAR, including emergency braking, pedestrian detection, and collision avoidance. Front-facing cameras may also be used for ADAS functions and systems including Lane Departure Warnings ("LDW"), Autonomous Cruise Control ("ACC"), and/or other functions such as traffic sign recognition.

A variety of cameras may be used in a front-facing configuration, including, for example, a monocular camera platform that includes a complementary metal oxide semiconductor ("CMOS") color imager. Another example may be a wide-view camera(s) 870 that may be used to perceive objects coming into view from the periphery (e.g., pedestrians, crossing traffic or bicycles). Although only one wide-view camera is illustrated in FIG. 8B, there may be any number (including zero) of wide-view cameras 870 on the vehicle 800. In addition, any number of long-range camera(s) 898 (e.g., a long-view stereo camera pair) may be used for depth-based object detection, especially for objects for which a neural network has not yet been trained. The long-range camera(s) 898 may also be used for object detection and classification, as well as basic object tracking.

Any number of stereo cameras 868 may also be included in a front-facing configuration. In at least one embodiment, one or more of stereo camera(s) 868 may include an integrated control unit comprising a scalable processing unit, which may provide a programmable logic ("FPGA") and a multi-core micro-processor with an integrated Controller Area Network ("CAN") or Ethernet interface on a single chip. Such a unit may be used to generate a 3D map of the vehicle's environment, including a distance estimate for all the points in the image. An alternative stereo camera(s) 868 may include a compact stereo vision sensor(s) that may include two camera lenses (one each on the left and right) and an image processing chip that may measure the distance from the vehicle to the target object and use the generated information (e.g., metadata) to activate the autonomous emergency braking and lane departure warning functions. Other types of stereo camera(s) 868 may be used in addition to, or alternatively from, those described herein.

Cameras with a field of view that include portions of the environment to the side of the vehicle 800 (e.g., side-view cameras) may be used for surround view, providing information used to create and update the occupancy grid, as well as to generate side impact collision warnings. For example, surround camera(s) 874 (e.g., four surround cameras 874 as illustrated in FIG. 8B) may be positioned to on the vehicle 800. The surround camera(s) 874 may include wide-view camera(s) 870, fisheye camera(s), 360 degree camera(s), and/or the like. Four example, four fisheye cameras may be positioned on the vehicle's front, rear, and sides. In an alternative arrangement, the vehicle may use three surround camera(s) 874 (e.g., left, right, and rear), and may leverage one or more other camera(s) (e.g., a forward-facing camera) as a fourth surround view camera.

Cameras with a field of view that include portions of the environment to the rear of the vehicle 800 (e.g., rear-view cameras) may be used for park assistance, surround view, rear collision warnings, and creating and updating the occupancy grid. A wide variety of cameras may be used including, but not limited to, cameras that are also suitable as a front-facing camera(s) (e.g., long-range and/or mid-range camera(s) 898, stereo camera(s) 868), infrared camera(s) 872, etc.), as described herein.

Cameras with a field of view that include portions of the interior environment within the cabin of the vehicle 800 (e.g., one or more OMS sensor(s) 801) may be used as part of an occupant monitoring system (OMS) such as, but not limited to, a driver monitoring system (DMS). For example, OMS sensors (e.g., the OMS sensor(s) 801) may be used (e.g., by the controller(s) 836) to track an occupant's and/or driver's gaze direction, head pose, and/or blinking. This gaze information may be used to determine a level of attentiveness of the occupant or driver (e.g., to detect drowsiness, fatigue, and/or distraction), and/or to take responsive action to prevent harm to the occupant or operator. In some embodiments, data from OMS sensors may be used to enable gaze-controlled operations triggered by driver and/or non-driver occupants such as, but not limited to, adjusting cabin temperature and/or airflow, opening and closing windows, controlling cabin lighting, controlling entertainment systems, adjusting mirrors, adjusting seat positions, and/or other operations. In some embodiments, an OMS (e.g., OMS 350) may be used for applications such as determining when objects and/or occupants have been left behind in a vehicle cabin (e.g., by detecting occupant presence after the driver exits the vehicle). In some embodiments, OMS sensor(s) 801 may include the optical image sensors 305.

Figure 8C:
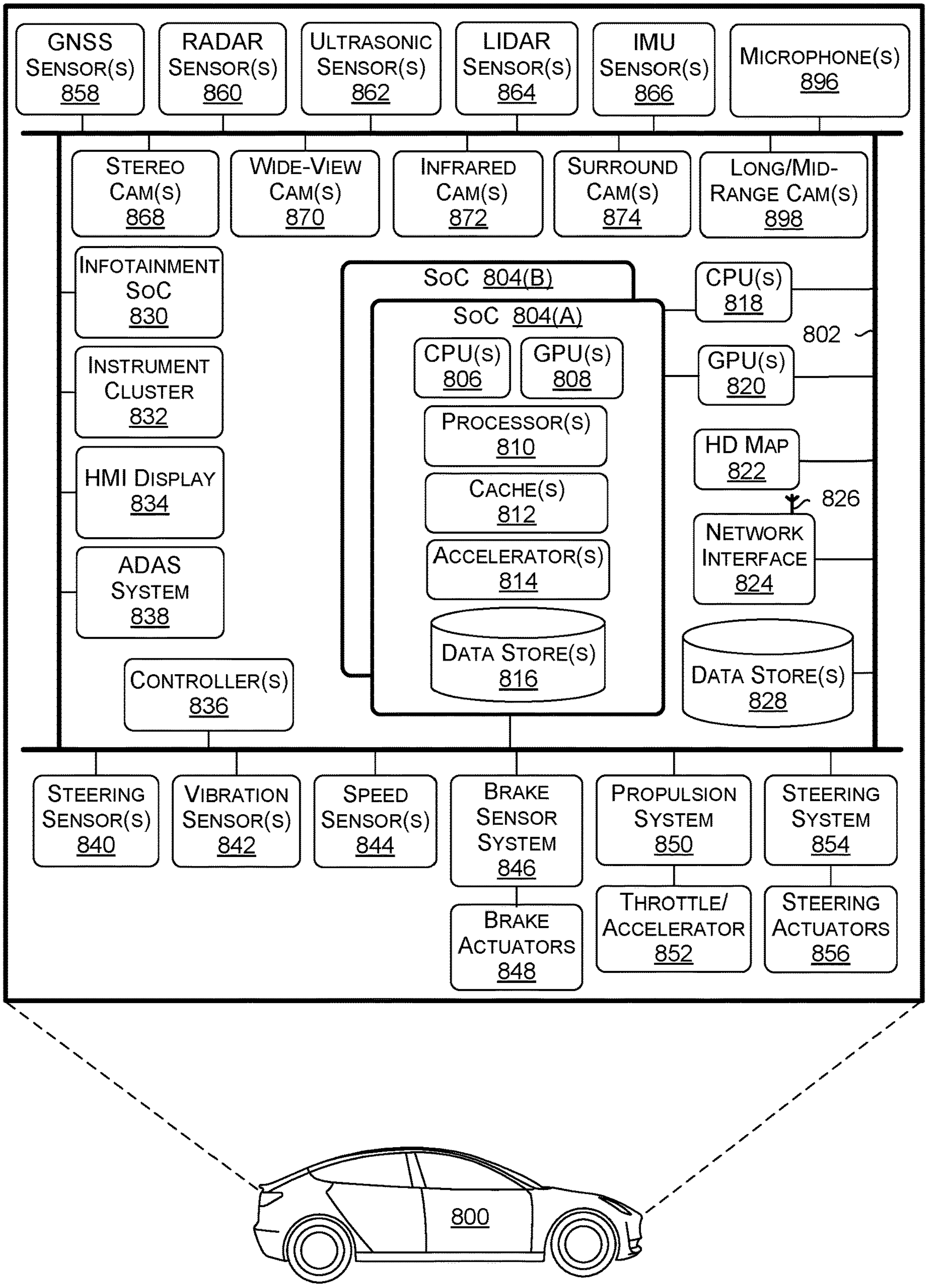
FIG. 8C is a block diagram of an example system architecture for the example autonomous vehicle of FIG. 8A, in accordance with some embodiments of the present disclosure.

FIG. 8C is a block diagram of an example system architecture for the example autonomous vehicle 800 of FIG. 8A, in accordance with some embodiments of the present disclosure. It should be understood that this and other arrangements described herein are set forth only as examples. Other arrangements and elements (e.g., machines, interfaces, functions, orders, groupings of functions, etc.) may be used in addition to or instead of those shown, and some elements may be omitted altogether. Further, many of the elements described herein are functional entities that may be implemented as discrete or distributed components or in conjunction with other components, and in any suitable combination and location. Various functions described herein as being performed by entities may be carried out by hardware, firmware, and/or software. For instance, various functions may be carried out by a processor executing instructions stored in memory.

Each of the components, features, and systems of the vehicle 800 in FIG. 8C are illustrated as being connected via bus 802. The bus 802 may include a Controller Area Network (CAN) data interface (alternatively referred to herein as a "CAN bus"). A CAN may be a network inside the vehicle 800 used to aid in control of various features and functionality of the vehicle 800, such as actuation of brakes, acceleration, braking, steering, windshield wipers, etc. A CAN bus may be configured to have dozens or even hundreds of nodes, each with its own unique identifier (e.g., a CAN ID). The CAN bus may be read to find steering wheel angle, ground speed, engine revolutions per minute (RPMs), button positions, and/or other vehicle status indicators. The CAN bus may be ASIL B compliant.

Although the bus 802 is described herein as being a CAN bus, this is not intended to be limiting. For example, in addition to, or alternatively from, the CAN bus, FlexRay and/or Ethernet may be used. Additionally, although a single line is used to represent the bus 802, this is not intended to be limiting. For example, there may be any number of busses 802, which may include one or more CAN busses, one or more FlexRay busses, one or more Ethernet busses, and/or one or more other types of busses using a different protocol. In some examples, two or more busses 802 may be used to perform different functions, and/or may be used for redundancy. For example, a first bus 802 may be used for collision avoidance functionality and a second bus 802 may be used for actuation control. In any example, each bus 802 may communicate with any of the components of the vehicle 800, and two or more busses 802 may communicate with the same components. In some examples, each SoC 804, each controller 836, and/or each computer within the vehicle may have access to the same input data (e.g., inputs from sensors of the vehicle 800), and may be connected to a common bus, such as the CAN bus.

The vehicle 800 may include one or more controller(s) 836, such as those described herein with respect to FIG. 8A. The controller(s) 836 may be used for a variety of functions. The controller(s) 836 may be coupled to any of the various other components and systems of the vehicle 800, and may be used for control of the vehicle 800, artificial intelligence of the vehicle 800, infotainment for the vehicle 800, and/or the like.

The vehicle 800 may include a system(s) on a chip (SoC) 804. The SoC 804 may include CPU(s) 806, GPU(s) 808, processor(s) 810, cache(s) 812, accelerator(s) 814, data store(s) 816, and/or other components and features not illustrated. The SoC(s) 804 may be used to control the vehicle 800 in a variety of platforms and systems. For example, the SoC(s) 804 may be combined in a system (e.g., the system of the vehicle 800) with an HD map 822 which may obtain map refreshes and/or updates via a network interface 824 from one or more servers (e.g., server(s) 878 of FIG. 8D).

The CPU(s) 806 may include a CPU cluster or CPU complex (alternatively referred to herein as a "CCPLEX"). The CPU(s) 806 may include multiple cores and/or L2 caches. For example, in some embodiments, the CPU(s) 806 may include eight cores in a coherent multi-processor configuration. In some embodiments, the CPU(s) 806 may include four dual-core clusters where each cluster has a dedicated L2 cache (e.g., a 2 MB L2 cache). The CPU(s) 806 (e.g., the CCPLEX) may be configured to support simultaneous cluster operation enabling any combination of the clusters of the CPU(s) 806 to be active at any given time.

The CPU(s) 806 may implement power management capabilities that include one or more of the following features: individual hardware blocks may be clock-gated automatically when idle to save dynamic power; each core clock may be gated when the core is not actively executing instructions due to execution of WFI/WFE instructions; each core may be independently power-gated; each core cluster may be independently clock-gated when all cores are clock-gated or power-gated; and/or each core cluster may be independently power-gated when all cores are power-gated. The CPU(s) 806 may further implement an enhanced algorithm for managing power states, where allowed power states and expected wakeup times are specified, and the hardware/microcode determines the best power state to enter for the core, cluster, and CCPLEX. The processing cores may support simplified power state entry sequences in software with the work offloaded to microcode. In some embodiments, one or more aspects and/or functions described with respect to any of the circadian rhythm-based drowsiness detection systems described herein may be implemented at least in part by CPU(s) 806.

The GPU(s) 808 may include an integrated GPU (alternatively referred to herein as an "iGPU"). The GPU(s) 808 may be programmable and may be efficient for parallel workloads. The GPU(s) 808, in some examples, may use an enhanced tensor instruction set. The GPU(s) 808 may include one or more streaming microprocessors, where each streaming microprocessor may include an L1 cache (e.g., an L1 cache with at least 96 KB storage capacity), and two or more of the streaming microprocessors may share an L2 cache (e.g., an L2 cache with a 512 KB storage capacity). In some embodiments, the GPU(s) 808 may include at least eight streaming microprocessors. The GPU(s) 808 may use compute application programming interface(s) (API(s)). In addition, the GPU(s) 808 may use one or more parallel computing platforms and/or programming models (e.g., NVIDIA's CUDA). In some embodiments, the drowsiness machine learning model 312 may be implemented at least in part by one or more of the GPU(s) 808.

The GPU(s) 808 may be power-optimized for best performance in automotive and embedded use cases. For example, the GPU(s) 808 may be fabricated on a Fin field-effect transistor (FinFET). However, this is not intended to be limiting and the GPU(s) 808 may be fabricated using other semiconductor manufacturing processes. Each streaming microprocessor may incorporate a number of mixed-precision processing cores partitioned into multiple blocks. For example, and without limitation, 64 PF32 cores and 32 PF64 cores may be partitioned into four processing blocks. In such an example, each processing block may be allocated 16 FP32 cores, 8 FP64 cores, 16 INT32 cores, two mixed-precision NVIDIA TENSOR COREs for deep learning matrix arithmetic, an L0 instruction cache, a warp scheduler, a dispatch unit, and/or a 64 KB register file. In addition, the streaming microprocessors may include independent parallel integer and floating-point data paths to provide for efficient execution of workloads with a mix of computation and addressing calculations. The streaming microprocessors may include independent thread scheduling capability to enable finer-grain synchronization and cooperation between parallel threads. The streaming microprocessors may include a combined L1 data cache and shared memory unit in order to improve performance while simplifying programming.

The GPU(s) 808 may include a high bandwidth memory (HBM) and/or a 16 GB HBM2 memory subsystem to provide, in some examples, about 900 GB/second peak memory bandwidth. In some examples, in addition to, or alternatively from, the HBM memory, a synchronous graphics random-access memory (SGRAM) may be used, such as a graphics double data rate type five synchronous random-access memory (GDDR5).

The GPU(s) 808 may include unified memory technology including access counters to allow for more accurate migration of memory pages to the processor that accesses them most frequently, thereby improving efficiency for memory ranges shared between processors. In some examples, address translation services (ATS) support may be used to allow the GPU(s) 808 to access the CPU(s) 806 page tables directly. In such examples, when the GPU(s) 808 memory management unit (MMU) experiences a miss, an address translation request may be transmitted to the CPU(s) 806. In response, the CPU(s) 806 may look in its page tables for the virtual-to-physical mapping for the address and transmits the translation back to the GPU(s) 808. As such, unified memory technology may allow a single unified virtual address space for memory of both the CPU(s) 806 and the GPU(s) 808, thereby simplifying the GPU(s) 808 programming and porting of applications to the GPU(s) 808.

In addition, the GPU(s) 808 may include an access counter that may keep track of the frequency of access of the GPU(s) 808 to memory of other processors. The access counter may help ensure that memory pages are moved to the physical memory of the processor that is accessing the pages most frequently.

The SoC(s) 804 may include any number of cache(s) 812, including those described herein. For example, the cache(s) 812 may include an L3 cache that is available to both the CPU(s) 806 and the GPU(s) 808 (e.g., that is connected both the CPU(s) 806 and the GPU(s) 808). The cache(s) 812 may include a write-back cache that may keep track of states of lines, such as by using a cache coherence protocol (e.g., MEI, MESI, MSI, etc.). The L3 cache may include 4 MB or more, depending on the embodiment, although smaller cache sizes may be used.

The SoC(s) 804 may include an arithmetic logic unit(s) (ALU(s)) which may be leveraged in performing processing with respect to any of the variety of tasks or operations of the vehicle 800—such as processing DNNs. In addition, the SoC(s) 804 may include a floating point unit(s) (FPU(s))—or other math coprocessor or numeric coprocessor types—for performing mathematical operations within the system. For example, the SoC(s) 804 may include one or more FPUs integrated as execution units within a CPU(s) 806 and/or GPU(s) 808.

The SoC(s) 804 may include one or more accelerators 814 (e.g., hardware accelerators, software accelerators, or a combination thereof). For example, the SoC(s) 804 may include a hardware acceleration cluster that may include optimized hardware accelerators and/or large on-chip memory. The large on-chip memory (e.g., 4 MB of SRAM), may enable the hardware acceleration cluster to accelerate neural networks and other calculations. The hardware acceleration cluster may be used to complement the GPU(s) 808 and to off-load some of the tasks of the GPU(s) 808 (e.g., to free up more cycles of the GPU(s) 808 for performing other tasks). As an example, the accelerator(s) 814 may be used for targeted workloads (e.g., perception, convolutional neural networks (CNNs), etc.) that are stable enough to be amenable to acceleration. The term "CNN," as used herein, may include all types of CNNs, including region-based or regional convolutional neural networks (RCNNs) and Fast RCNNs (e.g., as used for object detection).

The accelerator(s) 814 (e.g., the hardware acceleration cluster) may include a deep learning accelerator(s) (DLA). The DLA(s) may include one or more Tensor processing units (TPUs) that may be configured to provide an additional ten trillion operations per second for deep learning applications and inferencing. The TPUs may be accelerators configured to, and optimized for, performing image processing functions (e.g., for CNNs, RCNNs, etc.). The DLA(s) may further be optimized for a specific set of neural network types and floating point operations, as well as inferencing. The design of the DLA(s) may provide more performance per millimeter than a general-purpose GPU, and vastly exceeds the performance of a CPU. The TPU(s) may perform several functions, including a single-instance convolution function, supporting, for example, INT8, INT16, and FP16 data types for both features and weights, as well as post-processor functions.

The DLA(s) may quickly and efficiently execute neural networks, especially CNNs, on processed or unprocessed data for any of a variety of functions, including, for example and without limitation: a CNN for object identification and detection using data from camera sensors; a CNN for distance estimation using data from camera sensors; a CNN for emergency vehicle detection and identification and detection using data from microphones; a CNN for facial recognition and vehicle owner identification using data from camera sensors; and/or a CNN for security and/or safety related events.

The DLA(s) may perform any function of the GPU(s) 808, and by using an inference accelerator, for example, a designer may target either the DLA(s) or the GPU(s) 808 for any function. For example, the designer may focus processing of CNNs and floating point operations on the DLA(s) and leave other functions to the GPU(s) 808 and/or other accelerator(s) 814.

The accelerator(s) 814 (e.g., the hardware acceleration cluster) may include a programmable vision accelerator(s) (PVA), which may alternatively be referred to herein as a computer vision accelerator. The PVA(s) may be designed and configured to accelerate computer vision algorithms for the advanced driver assistance systems (ADAS), autonomous driving, and/or augmented reality (AR) and/or virtual reality (VR) applications. The PVA(s) may provide a balance between performance and flexibility. For example, each PVA(s) may include, for example and without limitation, any number of reduced instruction set computer (RISC) cores, direct memory access (DMA), and/or any number of vector processors.

The RISC cores may interact with image sensors (e.g., the image sensors of any of the cameras described herein), image signal processor(s), and/or the like. Each of the RISC cores may include any amount of memory. The RISC cores may use any of a number of protocols, depending on the embodiment. In some examples, the RISC cores may execute a real-time operating system (RTOS). The RISC cores may be implemented using one or more integrated circuit devices, application specific integrated circuits (ASICs), and/or memory devices. For example, the RISC cores may include an instruction cache and/or a tightly coupled RAM.

The DMA may enable components of the PVA(s) to access the system memory independently of the CPU(s) 806. The DMA may support any number of features used to provide optimization to the PVA including, but not limited to, supporting multi-dimensional addressing and/or circular addressing. In some examples, the DMA may support up to six or more dimensions of addressing, which may include block width, block height, block depth, horizontal block stepping, vertical block stepping, and/or depth stepping.

The vector processors may be programmable processors that may be designed to efficiently and flexibly execute programming for computer vision algorithms and provide signal processing capabilities. In some examples, the PVA may include a PVA core and two vector processing subsystem partitions. The PVA core may include a processor subsystem, DMA engine(s) (e.g., two DMA engines), and/or other peripherals. The vector processing subsystem may operate as the primary processing engine of the PVA, and may include a vector processing unit (VPU), an instruction cache, and/or vector memory (e.g., VMEM). A VPU core may include a digital signal processor such as, for example, a single instruction, multiple data (SIMD), very long instruction word (VLIW) digital signal processor. The combination of the SIMD and VLIW may enhance throughput and speed.

Each of the vector processors may include an instruction cache and may be coupled to dedicated memory. As a result, in some examples, each of the vector processors may be configured to execute independently of the other vector processors. In other examples, the vector processors that are included in a particular PVA may be configured to employ data parallelism. For example, in some embodiments, the plurality of vector processors included in a single PVA may execute the same computer vision algorithm, but on different regions of an image. In other examples, the vector processors included in a particular PVA may simultaneously execute different computer vision algorithms, on the same image, or even execute different algorithms on sequential images or portions of an image. Among other things, any number of PVAs may be included in the hardware acceleration cluster and any number of vector processors may be included in each of the PVAs. In addition, the PVA(s) may include additional error correcting code (ECC) memory, to enhance overall system safety.

The accelerator(s) 814 (e.g., the hardware acceleration cluster) may include a computer vision network on-chip and SRAM, for providing a high-bandwidth, low latency SRAM for the accelerator(s) 814. In some examples, the on-chip memory may include at least 4 MB SRAM, consisting of, for example and without limitation, eight field-configurable memory blocks, that may be accessible by both the PVA and the DLA. Each pair of memory blocks may include an advanced peripheral bus (APB) interface, configuration circuitry, a controller, and a multiplexer. Any type of memory may be used. The PVA and DLA may access the memory via a backbone that provides the PVA and DLA with high-speed access to memory. The backbone may include a computer vision network on-chip that interconnects the PVA and the DLA to the memory (e.g., using the APB).

The computer vision network on-chip may include an interface that determines, before transmission of any control signal/address/data, that both the PVA and the DLA provide ready and valid signals. Such an interface may provide for separate phases and separate channels for transmitting control signals/addresses/data, as well as burst-type communications for continuous data transfer. This type of interface may comply with ISO 26262 or IEC 61508 standards, although other standards and protocols may be used.

In some examples, the SoC(s) 804 may include a real-time ray-tracing hardware accelerator, such as described in U.S. patent application Ser. No. 16/101,232, filed on Aug. 10, 2018. The real-time ray-tracing hardware accelerator may be used to quickly and efficiently determine the positions and extents of objects (e.g., within a world model), to generate real-time visualization simulations, for RADAR signal interpretation, for sound propagation synthesis and/or analysis, for simulation of SONAR systems, for general wave propagation simulation, for comparison to LIDAR data for purposes of localization and/or other functions, and/or for other uses. In some embodiments, one or more tree traversal units (TTUs) may be used for executing one or more ray-tracing related operations.

The accelerator(s) 814 (e.g., the hardware accelerator cluster) have a wide array of uses for autonomous driving. The PVA may be a programmable vision accelerator that may be used for key processing stages in ADAS and autonomous vehicles. The PVA's capabilities are a good match for algorithmic domains needing predictable processing, at low power and low latency. In other words, the PVA performs well on semi-dense or dense regular computation, even on small data sets, which need predictable run-times with low latency and low power. Thus, in the context of platforms for autonomous vehicles, the PVAs are designed to run classic computer vision algorithms, as they are efficient at object detection and operating on integer math.

For example, according to one embodiment of the technology, the PVA is used to perform computer stereo vision. A semi-global matching-based algorithm may be used in some examples, although this is not intended to be limiting. Many applications for Level 3-5 autonomous driving require motion estimation/stereo matching on-the-fly (e.g., structure from motion, pedestrian recognition, lane detection, etc.). The PVA may perform computer stereo vision function on inputs from two monocular cameras.

In some examples, the PVA may be used to perform dense optical flow. According to process raw RADAR data (e.g., using a 4D Fast Fourier Transform) to provide Processed RADAR. In other examples, the PVA is used for time of flight depth processing, by processing raw time of flight data to provide processed time of flight data, for example.

The DLA may be used to run any type of network to enhance control and driving safety, including for example, a neural network that outputs a measure of confidence for each object detection. Such a confidence value may be interpreted as a probability, or as providing a relative "weight" of each detection compared to other detections. This confidence value enables the system to make further decisions regarding which detections should be considered as true positive detections rather than false positive detections. For example, the system may set a threshold value for the confidence and consider only the detections exceeding the threshold value as true positive detections. In an automatic emergency braking (AEB) system, false positive detections would cause the vehicle to automatically perform emergency braking, which is obviously undesirable. Therefore, only the most confident detections should be considered as triggers for AEB. The DLA may run a neural network for regressing the confidence value. The neural network may take as its input at least some subset of parameters, such as bounding box dimensions, ground plane estimate obtained (e.g. from another subsystem), inertial measurement unit (IMU) sensor 866 output that correlates with the vehicle 800 orientation, distance, 3D location estimates of the object obtained from the neural network and/or other sensors (e.g., LIDAR sensor(s) 864 or RADAR sensor(s) 860), among others.

The SoC(s) 804 may include data store(s) 816 (e.g., memory). The data store(s) 816 may be on-chip memory of the SoC(s) 804, which may store neural networks to be executed on the GPU and/or the DLA. In some examples, the data store(s) 816 may be large enough in capacity to store multiple instances of neural networks for redundancy and safety. The data store(s) 816 may comprise L2 or L3 cache(s) 812. Reference to the data store(s) 816 may include reference to the memory associated with the PVA, DLA, and/or other accelerator(s) 814, as described herein.

The SoC(s) 804 may include one or more processor(s) 810 (e.g., embedded processors). The processor(s) 810 may include a boot and power management processor that may be a dedicated processor and subsystem to handle boot power and management functions and related security enforcement. The boot and power management processor may be a part of the SoC(s) 804 boot sequence and may provide runtime power management services. The boot power and management processor may provide clock and voltage programming, assistance in system low power state transitions, management of SoC(s) 804 thermals and temperature sensors, and/or management of the SoC(s) 804 power states. Each temperature sensor may be implemented as a ring-oscillator whose output frequency is proportional to temperature, and the SoC(s) 804 may use the ring-oscillators to detect temperatures of the CPU(s) 806, GPU(s) 808, and/or accelerator(s) 814. If temperatures are determined to exceed a threshold, the boot and power management processor may enter a temperature fault routine and put the SoC(s) 804 into a lower power state and/or put the vehicle 800 into a chauffeur to safe stop mode (e.g., bring the vehicle 800 to a safe stop).

The processor(s) 810 may further include a set of embedded processors that may serve as an audio processing engine. The audio processing engine may be an audio subsystem that enables full hardware support for multi-channel audio over multiple interfaces, and a broad and flexible range of audio I/O interfaces. In some examples, the audio processing engine is a dedicated processor core with a digital signal processor with dedicated RAM.

The processor(s) 810 may further include an always on processor engine that may provide necessary hardware features to support low power sensor management and wake use cases. The always on processor engine may include a processor core, a tightly coupled RAM, supporting peripherals (e.g., timers and interrupt controllers), various I/O controller peripherals, and routing logic.

The processor(s) 810 may further include a safety cluster engine that includes a dedicated processor subsystem to handle safety management for automotive applications. The safety cluster engine may include two or more processor cores, a tightly coupled RAM, support peripherals (e.g., timers, an interrupt controller, etc.), and/or routing logic. In a safety mode, the two or more cores may operate in a lockstep mode and function as a single core with comparison logic to detect any differences between their operations.

The processor(s) 810 may further include a real-time camera engine that may include a dedicated processor subsystem for handling real-time camera management.

The processor(s) 810 may further include a high-dynamic range signal processor that may include an image signal processor that is a hardware engine that is part of the camera processing pipeline. In some embodiments, video sensor data 310 may be processed by the camera processing pipeline prior to input to the drowsiness machine learning model 312.

The processor(s) 810 may include a video image compositor that may be a processing block (e.g., implemented on a microprocessor) that implements video post-processing functions needed by a video playback application to produce the final image for the player window. The video image compositor may perform lens distortion correction on wide-view camera(s) 870, surround camera(s) 874, and/or on in-cabin monitoring camera sensors. In-cabin monitoring camera sensor is preferably monitored by a neural network running on another instance of the Advanced SoC, configured to identify in cabin events and respond accordingly. An in-cabin system may perform lip reading to activate cellular service and place a phone call, dictate emails, change the vehicle's destination, activate or change the vehicle's infotainment system and settings, or provide voice-activated web surfing. Certain functions are available to the driver only when the vehicle is operating in an autonomous mode, and are disabled otherwise.

The video image compositor may include enhanced temporal noise reduction for both spatial and temporal noise reduction. For example, where motion occurs in a video, the noise reduction weights spatial information appropriately, decreasing the weight of information provided by adjacent frames. Where an image or portion of an image does not include motion, the temporal noise reduction performed by the video image compositor may use information from the previous image to reduce noise in the current image.

The video image compositor may also be configured to perform stereo rectification on input stereo lens frames. The video image compositor may further be used for user interface composition when the operating system desktop is in use, and the GPU(s) 808 is not required to continuously render new surfaces. Even when the GPU(s) 808 is powered on and active doing 3D rendering, the video image compositor may be used to offload the GPU(s) 808 to improve performance and responsiveness.

The SoC(s) 804 may further include a mobile industry processor interface (MIPI) camera serial interface for receiving video and input from cameras, a high-speed interface, and/or a video input block that may be used for camera and related pixel input functions. The SoC(s) 804 may further include an input/output controller(s) that may be controlled by software and may be used for receiving I/O signals that are uncommitted to a specific role.

The SoC(s) 804 may further include a broad range of peripheral interfaces to enable communication with peripherals, audio codecs, power management, and/or other devices. The SoC(s) 804 may be used to process data from cameras (e.g., connected over Gigabit Multimedia Serial Link and Ethernet), sensors (e.g., LIDAR sensor(s) 864, RADAR sensor(s) 860, etc. that may be connected over Ethernet), data from bus 802 (e.g., speed of vehicle 800, steering wheel position, etc.), data from GNSS sensor(s) 858 (e.g., connected over Ethernet or CAN bus). The SoC(s) 804 may further include dedicated high-performance mass storage controllers that may include their own DMA engines, and that may be used to free the CPU(s) 806 from routine data management tasks.

The SoC(s) 804 may be an end-to-end platform with a flexible architecture that spans automation levels 3-5, thereby providing a comprehensive functional safety architecture that leverages and makes efficient use of computer vision and ADAS techniques for diversity and redundancy, provides a platform for a flexible, reliable driving software stack, along with deep learning tools. The SoC(s) 804 may be faster, more reliable, and even more energy-efficient and space-efficient than conventional systems. For example, the accelerator(s) 814, when combined with the CPU(s) 806, the GPU(s) 808, and the data store(s) 816, may provide for a fast, efficient platform for level 3-5 autonomous vehicles.

The technology thus provides capabilities and functionality that cannot be achieved by conventional systems. For example, computer vision algorithms may be executed on CPUs, which may be configured using high-level programming language, such as the C programming language, to execute a wide variety of processing algorithms across a wide variety of visual data. However, CPUs are oftentimes unable to meet the performance requirements of many computer vision applications, such as those related to execution time and power consumption, for example. In particular, many CPUs are unable to execute complex object detection algorithms in real-time, which is a requirement of in-vehicle ADAS applications, and a requirement for practical Level 3-5 autonomous vehicles.

In contrast to conventional systems, by providing a CPU complex, GPU complex, and a hardware acceleration cluster, the technology described herein allows for multiple neural networks to be performed simultaneously and/or sequentially, and for the results to be combined together to enable Level 3-5 autonomous driving functionality. For example, a CNN executing on the DLA or dGPU (e.g., the GPU(s) 820) may include a text and word recognition, allowing the supercomputer to read and understand traffic signs, including signs for which the neural network has not been specifically trained. The DLA may further include a neural network that is able to identify, interpret, and provides semantic understanding of the sign, and to pass that semantic understanding to the path planning modules running on the CPU Complex.

As another example, multiple neural networks may be run simultaneously, as is required for Level 3, 4, or 5 driving. For example, a warning sign consisting of "Caution: flashing lights indicate icy conditions," along with an electric light, may be independently or collectively interpreted by several neural networks. The sign itself may be identified as a traffic sign by a first deployed neural network (e.g., a neural network that has been trained), the text "Flashing lights indicate icy conditions" may be interpreted by a second deployed neural network, which informs the vehicle's path planning software (preferably executing on the CPU Complex) that when flashing lights are detected, icy conditions exist. The flashing light may be identified by operating a third deployed neural network over multiple frames, informing the vehicle's path-planning software of the presence (or absence) of flashing lights. All three neural networks may run simultaneously, such as within the DLA and/or on the GPU(s) 808.

In some examples, a CNN for facial recognition and vehicle owner identification may use data from camera sensors to identify the presence of an authorized driver and/or owner of the vehicle 800. The always on sensor processing engine may be used to unlock the vehicle when the owner approaches the driver door and turn on the lights, and, in security mode, to disable the vehicle when the owner leaves the vehicle. In this way, the SoC(s) 804 provide for security against theft and/or carjacking.

In another example, a CNN for emergency vehicle detection and identification may use data from microphones 896 to detect and identify emergency vehicle sirens. In contrast to conventional systems, that use general classifiers to detect sirens and manually extract features, the SoC(s) 804 use the CNN for classifying environmental and urban sounds, as well as classifying visual data. In a preferred embodiment, the CNN running on the DLA is trained to identify the relative closing speed of the emergency vehicle (e.g., by using the Doppler Effect). The CNN may also be trained to identify emergency vehicles specific to the local area in which the vehicle is operating, as identified by GNSS sensor(s) 858. Thus, for example, when operating in Europe the CNN will seek to detect European sirens, and when in the United States the CNN will seek to identify only North American sirens. Once an emergency vehicle is detected, a control program may be used to execute an emergency vehicle safety routine, slowing the vehicle, pulling over to the side of the road, parking the vehicle, and/or idling the vehicle, with the assistance of ultrasonic sensors 862, until the emergency vehicle(s) passes.

The vehicle may include a CPU(s) 818 (e.g., discrete CPU(s), or dCPU(s)), that may be coupled to the SoC(s) 804 via a high-speed interconnect (e.g., PCIe). The CPU(s) 818 may include an X86 processor, for example. The CPU(s) 818 may be used to perform any of a variety of functions, including arbitrating potentially inconsistent results between ADAS sensors and the SoC(s) 804, and/or monitoring the status and health of the controller(s) 836 and/or infotainment SoC 830, for example.

The vehicle 800 may include a GPU(s) 820 (e.g., discrete GPU(s), or dGPU(s)), that may be coupled to the SoC(s) 804 via a high-speed interconnect (e.g., NVIDIA's NVLINK). The GPU(s) 820 may provide additional artificial intelligence functionality, such as by executing redundant and/or different neural networks, and may be used to train and/or update neural networks based on input (e.g., sensor data) from sensors of the vehicle 800.

The vehicle 800 may further include the network interface 824 which may include one or more wireless antennas 826 (e.g., one or more wireless antennas for different communication protocols, such as a cellular antenna, a Bluetooth antenna, etc.). The network interface 824 may be used to enable wireless connectivity over the Internet with the cloud (e.g., with the server(s) 878 and/or other network devices), with other vehicles, and/or with computing devices (e.g., client devices of passengers). To communicate with other vehicles, a direct link may be established between the two vehicles and/or an indirect link may be established (e.g., across networks and over the Internet). Direct links may be provided using a vehicle-to-vehicle communication link. The vehicle-to-vehicle communication link may provide the vehicle 800 information about vehicles in proximity to the vehicle 800 (e.g., vehicles in front of, on the side of, and/or behind the vehicle 800). This functionality may be part of a cooperative adaptive cruise control functionality of the vehicle 800.

The network interface 824 may include a SoC that provides modulation and demodulation functionality and enables the controller(s) 836 to communicate over wireless networks. The network interface 824 may include a radio frequency front-end for up-conversion from baseband to radio frequency, and down conversion from radio frequency to baseband. The frequency conversions may be performed through well-known processes, and/or may be performed using super-heterodyne processes. In some examples, the radio frequency front end functionality may be provided by a separate chip. The network interface may include wireless functionality for communicating over LTE, WCDMA, UMTS, GSM, CDMA2000, Bluetooth, Bluetooth LE, Wi-Fi, Z-Wave, ZigBee, LoRaWAN, and/or other wireless protocols.

The vehicle 800 may further include data store(s) 828 which may include off-chip (e.g., off the SoC(s) 804) storage. The data store(s) 828 may include one or more storage elements including RAM, SRAM, DRAM, VRAM, Flash, hard disks, and/or other components and/or devices that may store at least one bit of data.

The vehicle 800 may further include GNSS sensor(s) 858. The GNSS sensor(s) 858 (e.g., GPS, assisted GPS sensors, differential GPS (DGPS) sensors, etc.), to assist in mapping, perception, occupancy grid generation, and/or path planning functions. Any number of GNSS sensor(s) 858 may be used, including, for example and without limitation, a GPS using a USB connector with an Ethernet to Serial (RS-232) bridge.

The vehicle 800 may further include RADAR sensor(s) 860. The RADAR sensor(s) 860 may be used by the vehicle 800 for long-range vehicle detection, even in darkness and/or severe weather conditions. RADAR functional safety levels may be ASIL B. The RADAR sensor(s) 860 may use the CAN and/or the bus 802 (e.g., to transmit data generated by the RADAR sensor(s) 860) for control and to access object tracking data, with access to Ethernet to access raw data in some examples. A wide variety of RADAR sensor types may be used. For example, and without limitation, the RADAR sensor(s) 860 may be suitable for front, rear, and side RADAR use. In some example, Pulse Doppler RADAR sensor(s) are used.

The RADAR sensor(s) 860 may include different configurations, such as long range with narrow field of view, short range with wide field of view, short range side coverage, etc. In some examples, long-range RADAR may be used for adaptive cruise control functionality. The long-range RADAR systems may provide a broad field of view realized by two or more independent scans, such as within a 250 m range. The RADAR sensor(s) 860 may help in distinguishing between static and moving objects, and may be used by ADAS systems for emergency brake assist and forward collision warning. Long-range RADAR sensors may include monostatic multimodal RADAR with multiple (e.g., six or more) fixed RADAR antennae and a high-speed CAN and FlexRay interface. In an example with six antennae, the central four antennae may create a focused beam pattern, designed to record the vehicle's 800 surroundings at higher speeds with minimal interference from traffic in adjacent lanes. The other two antennae may expand the field of view, making it possible to quickly detect vehicles entering or leaving the vehicle's 800 lane.

Mid-range RADAR systems may include, as an example, a range of up to 860 m (front) or 80 m (rear), and a field of view of up to 42 degrees (front) or 850 degrees (rear). Short-range RADAR systems may include, without limitation, RADAR sensors designed to be installed at both ends of the rear bumper. When installed at both ends of the rear bumper, such a RADAR sensor systems may create two beams that constantly monitor the blind spot in the rear and next to the vehicle.

Short-range RADAR systems may be used in an ADAS system for blind spot detection and/or lane change assist.

The vehicle 800 may further include ultrasonic sensor(s) 862. The ultrasonic sensor(s) 862, which may be positioned at the front, back, and/or the sides of the vehicle 800, may be used for park assist and/or to create and update an occupancy grid. A wide variety of ultrasonic sensor(s) 862 may be used, and different ultrasonic sensor(s) 862 may be used for different ranges of detection (e.g., 2.5 m, 4 m). The ultrasonic sensor(s) 862 may operate at functional safety levels of ASIL B.

The vehicle 800 may include LIDAR sensor(s) 864. The LIDAR sensor(s) 864 may be used for object and pedestrian detection, emergency braking, collision avoidance, and/or other functions. The LIDAR sensor(s) 864 may be functional safety level ASIL B. In some examples, the vehicle 800 may include multiple LIDAR sensors 864 (e.g., two, four, six, etc.) that may use Ethernet (e.g., to provide data to a Gigabit Ethernet switch).

In some examples, the LIDAR sensor(s) 864 may be capable of providing a list of objects and their distances for a 360-degree field of view. Commercially available LIDAR sensor(s) 864 may have an advertised range of approximately 800 m, with an accuracy of 2 cm-3 cm, and with support for a 800 Mbps Ethernet connection, for example. In some examples, one or more non-protruding LIDAR sensors 864 may be used. In such examples, the LIDAR sensor(s) 864 may be implemented as a small device that may be embedded into the front, rear, sides, and/or corners of the vehicle 800. The LIDAR sensor(s) 864, in such examples, may provide up to a 120-degree horizontal and 35-degree vertical field-of-view, with a 200 m range even for low-reflectivity objects. Front-mounted LIDAR sensor(s) 864 may be configured for a horizontal field of view between 45 degrees and 135 degrees.

In some examples, LIDAR technologies, such as 3D flash LIDAR, may also be used. 3D Flash LIDAR uses a flash of a laser as a transmission source, to illuminate vehicle surroundings up to approximately 200 m. A flash LIDAR unit includes a receptor, which records the laser pulse transit time and the reflected light on each pixel, which in turn corresponds to the range from the vehicle to the objects. Flash LIDAR may allow for highly accurate and distortion-free images of the surroundings to be generated with every laser flash. In some examples, four flash LIDAR sensors may be deployed, one at each side of the vehicle 800. Available 3D flash LIDAR systems include a solid-state 3D staring array LIDAR camera with no moving parts other than a fan (e.g., a non-scanning LIDAR device). The flash LIDAR device may use a 5 nanosecond class I (eye-safe) laser pulse per frame and may capture the reflected laser light in the form of 3D range point clouds and co-registered intensity data. By using flash LIDAR, and because flash LIDAR is a solid-state device with no moving parts, the LIDAR sensor(s) 864 may be less susceptible to motion blur, vibration, and/or shock.

The vehicle may further include IMU sensor(s) 866. The IMU sensor(s) 866 may be located at a center of the rear axle of the vehicle 800, in some examples. The IMU sensor(s) 866 may include, for example and without limitation, an accelerometer(s), a magnetometer(s), a gyroscope(s), a magnetic compass(es), and/or other sensor types. In some examples, such as in six-axis applications, the IMU sensor(s) 866 may include accelerometers and gyroscopes, while in nine-axis applications, the IMU sensor(s) 866 may include accelerometers, gyroscopes, and magnetometers.

In some embodiments, the IMU sensor(s) 866 may be implemented as a miniature, high performance GPS-Aided Inertial Navigation System (GPS/INS) that combines micro-electro-mechanical systems (MEMS) inertial sensors, a high-sensitivity GPS receiver, and advanced Kalman filtering algorithms to provide estimates of position, velocity, and attitude. As such, in some examples, the IMU sensor(s) 866 may enable the vehicle 800 to estimate heading without requiring input from a magnetic sensor by directly observing and correlating the changes in velocity from GPS to the IMU sensor(s) 866. In some examples, the IMU sensor(s) 866 and the GNSS sensor(s) 858 may be combined in a single integrated unit.

The vehicle may include microphone(s) 896 placed in and/or around the vehicle 800. The microphone(s) 896 may be used for emergency vehicle detection and identification, among other things.

The vehicle may further include any number of camera types, including stereo camera(s) 868, wide-view camera(s) 870, infrared camera(s) 872, surround camera(s) 874, long-range and/or mid-range camera(s) 898, and/or other camera types. The cameras may be used to capture image data around an entire periphery of the vehicle 800. The types of cameras used depends on the embodiments and requirements for the vehicle 800, and any combination of camera types may be used to provide the necessary coverage around the vehicle 800. In addition, the number of cameras may differ depending on the embodiment. For example, the vehicle may include six cameras, seven cameras, ten cameras, twelve cameras, and/or another number of cameras. The cameras may support, as an example and without limitation, Gigabit Multimedia Serial Link (GMSL) and/or Gigabit Ethernet. Each of the camera(s) is described with more detail herein with respect to FIG. 8A and FIG. 8B.

The vehicle 800 may further include vibration sensor(s) 842. The vibration sensor(s) 842 may measure vibrations of components of the vehicle, such as the axle(s). For example, changes in vibrations may indicate a change in road surfaces. In another example, when two or more vibration sensors 842 are used, the differences between the vibrations may be used to determine friction or slippage of the road surface (e.g., when the difference in vibration is between a power-driven axle and a freely rotating axle).

The vehicle 800 may include an ADAS system 838. The ADAS system 838 may include a SoC, in some examples. The ADAS system 838 may include autonomous/adaptive/automatic cruise control (ACC), cooperative adaptive cruise control (CACC), forward crash warning (FCW), automatic emergency braking (AEB), lane departure warnings (LDW), lane keep assist (LKA), blind spot warning (BSW), rear cross-traffic warning (RCTW), collision warning systems (CWS), lane centering (LC), and/or other features and functionality.

The ACC systems may use RADAR sensor(s) 860, LIDAR sensor(s) 864, and/or a camera(s). The ACC systems may include longitudinal ACC and/or lateral ACC. Longitudinal ACC monitors and controls the distance to the vehicle immediately ahead of the vehicle 800 and automatically adjust the vehicle speed to maintain a safe distance from vehicles ahead. Lateral ACC performs distance keeping, and advises the vehicle 800 to change lanes when necessary. Lateral ACC is related to other ADAS applications such as LCA and CWS.

CACC uses information from other vehicles that may be received via the network interface 824 and/or the wireless antenna(s) 826 from other vehicles via a wireless link, or indirectly, over a network connection (e.g., over the Internet). Direct links may be provided by a vehicle-to-vehicle (V2V) communication link, while indirect links may be infrastructure-to-vehicle (12V) communication link. In general, the V2V communication concept provides information about the immediately preceding vehicles (e.g., vehicles immediately ahead of and in the same lane as the vehicle 800), while the 12V communication concept provides information about traffic further ahead. CACC systems may include either or both I2V and V2V information sources. Given the information of the vehicles ahead of the vehicle 800, CACC may be more reliable and it has potential to improve traffic flow smoothness and reduce congestion on the road.

FCW systems are designed to alert the driver to a hazard, so that the driver may take corrective action. FCW systems use a front-facing camera and/or RADAR sensor(s) 860, coupled to a dedicated processor, DSP, FPGA, and/or ASIC, that is electrically coupled to driver feedback, such as a display, speaker, and/or vibrating component. FCW systems may provide a warning, such as in the form of a sound, visual warning, vibration and/or a quick brake pulse.

AEB systems detect an impending forward collision with another vehicle or other object, and may automatically apply the brakes if the driver does not take corrective action within a specified time or distance parameter. AEB systems may use front-facing camera(s) and/or RADAR sensor(s) 860, coupled to a dedicated processor, DSP, FPGA, and/or ASIC. When the AEB system detects a hazard, it typically first alerts the driver to take corrective action to avoid the collision and, if the driver does not take corrective action, the AEB system may automatically apply the brakes in an effort to prevent, or at least mitigate, the impact of the predicted collision. AEB systems, may include techniques such as dynamic brake support and/or crash imminent braking.

LDW systems provide visual, audible, and/or tactile warnings, such as steering wheel or seat vibrations, to alert the driver when the vehicle 800 crosses lane markings. A LDW system does not activate when the driver indicates an intentional lane departure, by activating a turn signal. LDW systems may use front-side facing cameras, coupled to a dedicated processor, DSP, FPGA, and/or ASIC, that is electrically coupled to driver feedback, such as a display, speaker, and/or vibrating component.

LKA systems are a variation of LDW systems. LKA systems provide steering input or braking to correct the vehicle 800 if the vehicle 800 starts to exit the lane.

BSW systems detects and warn the driver of vehicles in an automobile's blind spot. BSW systems may provide a visual, audible, and/or tactile alert to indicate that merging or changing lanes is unsafe. The system may provide an additional warning when the driver uses a turn signal. BSW systems may use rear-side facing camera(s) and/or RADAR sensor(s) 860, coupled to a dedicated processor, DSP, FPGA, and/or ASIC, that is electrically coupled to driver feedback, such as a display, speaker, and/or vibrating component.

RCTW systems may provide visual, audible, and/or tactile notification when an object is detected outside the rear-camera range when the vehicle 800 is backing up. Some RCTW systems include AEB to ensure that the vehicle brakes are applied to avoid a crash. RCTW systems may use one or more rear-facing RADAR sensor(s) 860, coupled to a dedicated processor, DSP, FPGA, and/or ASIC, that is electrically coupled to driver feedback, such as a display, speaker, and/or vibrating component.

Conventional ADAS systems may be prone to false positive results which may be annoying and distracting to a driver, but typically are not catastrophic, because the ADAS systems alert the driver and allow the driver to decide whether a safety condition truly exists and act accordingly. However, in an autonomous vehicle 800, the vehicle 800 itself must, in the case of conflicting results, decide whether to heed the result from a primary computer or a secondary computer (e.g., a first controller 836 or a second controller 836). For example, in some embodiments, the ADAS system 838 may be a backup and/or secondary computer for providing perception information to a backup computer rationality module. The backup computer rationality monitor may run a redundant diverse software on hardware components to detect faults in perception and dynamic driving tasks. Outputs from the ADAS system 838 may be provided to a supervisory MCU. If outputs from the primary computer and the secondary computer conflict, the supervisory MCU must determine how to reconcile the conflict to ensure safe operation.

In some examples, the primary computer may be configured to provide the supervisory MCU with a confidence score, indicating the primary computer's confidence in the chosen result. If the confidence score exceeds a threshold, the supervisory MCU may follow the primary computer's direction, regardless of whether the secondary computer provides a conflicting or inconsistent result. Where the confidence score does not meet the threshold, and where the primary and secondary computer indicate different results (e.g., the conflict), the supervisory MCU may arbitrate between the computers to determine the appropriate outcome.

The supervisory MCU may be configured to run a neural network(s) that is trained and configured to determine, based on outputs from the primary computer and the secondary computer, conditions under which the secondary computer provides false alarms. Thus, the neural network(s) in the supervisory MCU may learn when the secondary computer's output may be trusted, and when it cannot. For example, when the secondary computer is a RADAR-based FCW system, a neural network(s) in the supervisory MCU may learn when the FCW system is identifying metallic objects that are not, in fact, hazards, such as a drainage grate or manhole cover that triggers an alarm. Similarly, when the secondary computer is a camera-based LDW system, a neural network in the supervisory MCU may learn to override the LDW when bicyclists or pedestrians are present and a lane departure is, in fact, the safest maneuver. In embodiments that include a neural network(s) running on the supervisory MCU, the supervisory MCU may include at least one of a DLA or GPU suitable for running the neural network(s) with associated memory. In preferred embodiments, the supervisory MCU may comprise and/or be included as a component of the SoC(s) 804.

In other examples, ADAS system 838 may include a secondary computer that performs ADAS functionality using traditional rules of computer vision. As such, the secondary computer may use classic computer vision rules (if-then), and the presence of a neural network(s) in the supervisory MCU may improve reliability, safety and performance. For example, the diverse implementation and intentional non-identity makes the overall system more fault-tolerant, especially to faults caused by software (or software-hardware interface) functionality. For example, if there is a software bug or error in the software running on the primary computer, and the non-identical software code running on the secondary computer provides the same overall result, the supervisory MCU may have greater confidence that the overall result is correct, and the bug in software or hardware on primary computer is not causing material error.

In some examples, the output of the ADAS system 838 may be fed into the primary computer's perception block and/or the primary computer's dynamic driving task block. For example, if the ADAS system 838 indicates a forward crash warning due to an object immediately ahead, the perception block may use this information when identifying objects. In other examples, the secondary computer may have its own neural network which is trained and thus reduces the risk of false positives, as described herein.

The vehicle 800 may further include the infotainment SoC 830 (e.g., an in-vehicle infotainment system (IVI)). Although illustrated and described as a SoC, the infotainment system may not be a SoC, and may include two or more discrete components. The infotainment SoC 830 may include a combination of hardware and software that may be used to provide audio (e.g., music, a personal digital assistant, navigational instructions, news, radio, etc.), video (e.g., TV, movies, streaming, etc.), phone (e.g., hands-free calling), network connectivity (e.g., LTE, Wi-Fi, etc.), and/or information services (e.g., navigation systems, rear-parking assistance, a radio data system, vehicle related information such as fuel level, total distance covered, brake fuel level, oil level, door open/close, air filter information, etc.) to the vehicle 800. For example, the infotainment SoC 830 may radios, disk players, navigation systems, video players, USB and Bluetooth connectivity, carputers, in-car entertainment, Wi-Fi, steering wheel audio controls, hands free voice control, a heads-up display (HUD), an HMI display 834, a telematics device, a control panel (e.g., for controlling and/or interacting with various components, features, and/or systems), and/or other components. The infotainment SoC 830 may further be used to provide information (e.g., visual and/or audible) to a user(s) of the vehicle, such as information from the ADAS system 838, autonomous driving information such as planned vehicle maneuvers, trajectories, surrounding environment information (e.g., intersection information, vehicle information, road information, etc.), and/or other information.

The infotainment SoC 830 may include GPU functionality. The infotainment SoC 830 may communicate over the bus 802 (e.g., CAN bus, Ethernet, etc.) with other devices, systems, and/or components of the vehicle 800. In some examples, the infotainment SoC 830 may be coupled to a supervisory MCU such that the GPU of the infotainment system may perform some self-driving functions in the event that the primary controller(s) 836 (e.g., the primary and/or backup computers of the vehicle 800) fail. In such an example, the infotainment SoC 830 may put the vehicle 800 into a chauffeur to safe stop mode, as described herein.

The vehicle 800 may further include an instrument cluster 832 (e.g., a digital dash, an electronic instrument cluster, a digital instrument panel, etc.). The instrument cluster 832 may include a controller and/or supercomputer (e.g., a discrete controller or supercomputer). The instrument cluster 832 may include a set of instrumentation such as a speedometer, fuel level, oil pressure, tachometer, odometer, turn indicators, gearshift position indicator, seat belt warning light(s), parking-brake warning light(s), engine-malfunction light(s), airbag (SRS) system information, lighting controls, safety system controls, navigation information, etc. In some examples, information may be displayed and/or shared among the infotainment SoC 830 and the instrument cluster 832. In other words, the instrument cluster 832 may be included as part of the infotainment SoC 830, or vice versa.

Figure 8D:
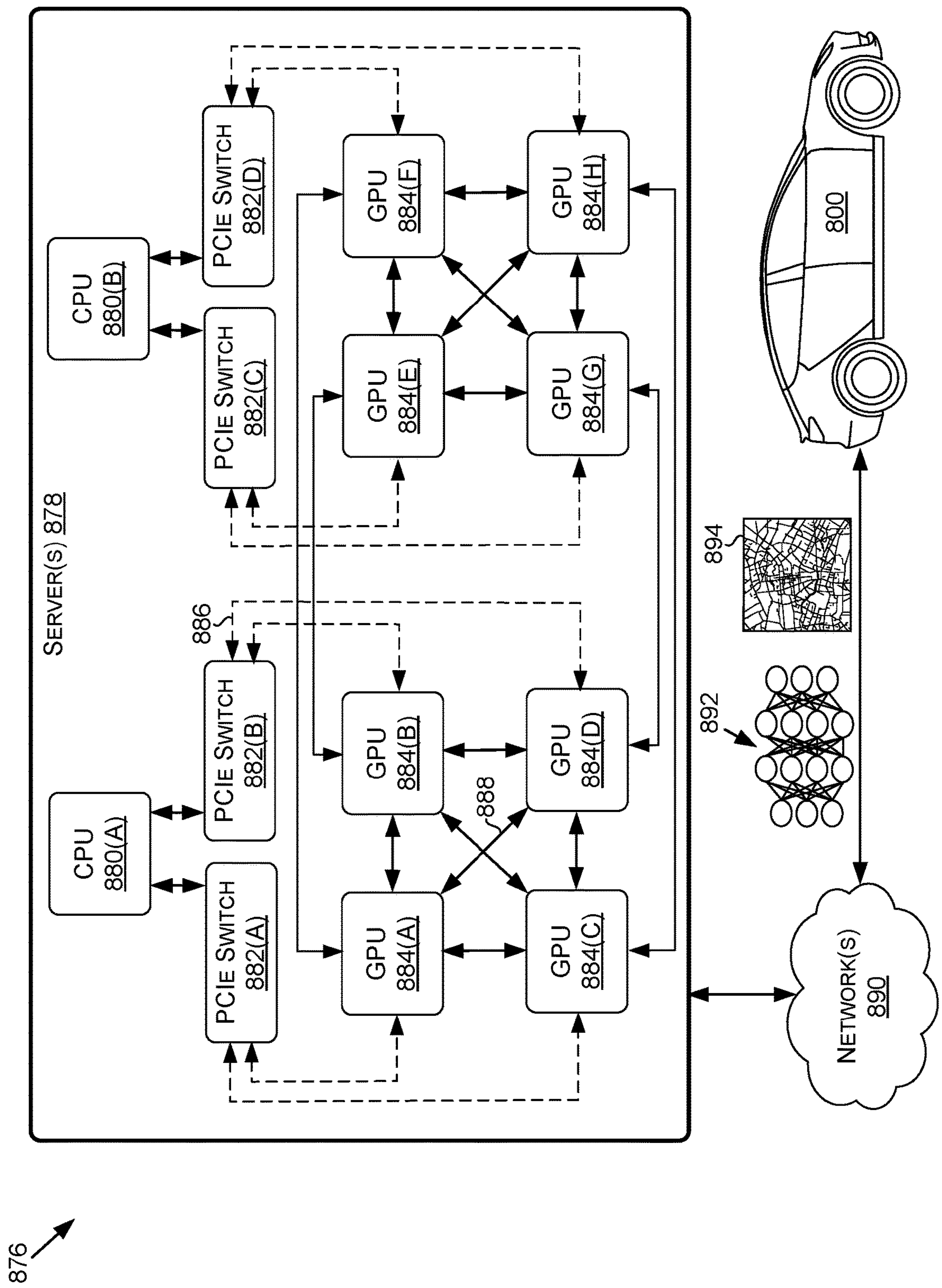
FIG. 8D is a system diagram for communication between cloud-based server(s) and the example autonomous vehicle of FIG. 8A, in accordance with some embodiments of the present disclosure.

FIG. 8D is a system diagram for communication between cloud-based server(s) and the example autonomous vehicle 800 of FIG. 8A, in accordance with some embodiments of the present disclosure. The system 876 may include server(s) 878, network(s) 890, and vehicles, including the vehicle 800. The server(s) 878 may include a plurality of GPUs 884(A)-884(H) (collectively referred to herein as GPUs 884), PCIe switches 882(A)-882(D) (collectively referred to herein as PCIe switches 882), and/or CPUs 880(A)-880(B) (collectively referred to herein as CPUs 880). The GPUs 884, the CPUs 880, and the PCIe switches may be interconnected with high-speed interconnects such as, for example and without limitation, NVLink interfaces 888 developed by NVIDIA and/or PCIe connections 886. In some examples, the GPUs 884 are connected via NVLink and/or NVSwitch SoC and the GPUs 884 and the PCIe switches 882 are connected via PCIe interconnects. Although eight GPUs 884, two CPUs 880, and two PCIe switches are illustrated, this is not intended to be limiting. Depending on the embodiment, each of the server(s) 878 may include any number of GPUs 884, CPUs 880, and/or PCIe switches. For example, the server(s) 878 may each include eight, sixteen, thirty-two, and/or more GPUs 884.

The server(s) 878 may receive, over the network(s) 890 and from the vehicles, image data representative of images showing unexpected or changed road conditions, such as recently commenced road-work. The server(s) 878 may transmit, over the network(s) 890 and to the vehicles, neural networks 892, updated neural networks 892, and/or map information 894, including information regarding traffic and road conditions. The updates to the map information 894 may include updates for the HD map 822, such as information regarding construction sites, potholes, detours, flooding, and/or other obstructions. In some examples, the neural networks 892, the updated neural networks 892, and/or the map information 894 may have resulted from new training and/or experiences represented in data received from any number of vehicles in the environment, and/or based on training performed at a datacenter (e.g., using the server(s) 878 and/or other servers).

The server(s) 878 may be used to train machine learning models (e.g., neural networks) based on training data. The training data may be generated by the vehicles, and/or may be generated in a simulation (e.g., using a game engine). In some examples, the training data is tagged (e.g., where the neural network benefits from supervised learning) and/or undergoes other pre-processing, while in other examples the training data is not tagged and/or pre-processed (e.g., where the neural network does not require supervised learning). Training may be executed according to any one or more classes of machine learning techniques, including, without limitation, classes such as: supervised training, semi-supervised training, unsupervised training, self-learning, reinforcement learning, federated learning, transfer learning, feature learning (including principal component and cluster analyses), multi-linear subspace learning, manifold learning, representation learning (including spare dictionary learning), rule-based machine learning, anomaly detection, and any variants or combinations therefor. Once the machine learning models are trained, the machine learning models may be used by the vehicles (e.g., transmitted to the vehicles over the network(s) 890, and/or the machine learning models may be used by the server(s) 878 to remotely monitor the vehicles.

In some examples, the server(s) 878 may receive data from the vehicles and apply the data to up-to-date real-time neural networks for real-time intelligent inferencing. The server(s) 878 may include deep-learning supercomputers and/or dedicated AI computers powered by GPU(s) 884, such as a DGX and DGX Station machines developed by NVIDIA. However, in some examples, the server(s) 878 may include deep learning infrastructure that use only CPU-powered datacenters.

The deep-learning infrastructure of the server(s) 878 may be capable of fast, real-time inferencing, and may use that capability to evaluate and verify the health of the processors, software, and/or associated hardware in the vehicle 800. For example, the deep-learning infrastructure may receive periodic updates from the vehicle 800, such as a sequence of images and/or objects that the vehicle 800 has located in that sequence of images (e.g., via computer vision and/or other machine learning object classification techniques). The deep-learning infrastructure may run its own neural network to identify the objects and compare them with the objects identified by the vehicle 800 and, if the results do not match and the infrastructure concludes that the AI in the vehicle 800 is malfunctioning, the server(s) 878 may transmit a signal to the vehicle 800 instructing a fail-safe computer of the vehicle 800 to assume control, notify the passengers, and complete a safe parking maneuver.

For inferencing, the server(s) 878 may include the GPU(s) 884 and one or more programmable inference accelerators (e.g., NVIDIA's TensorRT). The combination of GPU-powered servers and inference acceleration may make real-time responsiveness possible. In other examples, such as where performance is less critical, servers powered by CPUs, FPGAs, and other processors may be used for inferencing.

Example Computing Device

Figure 9:
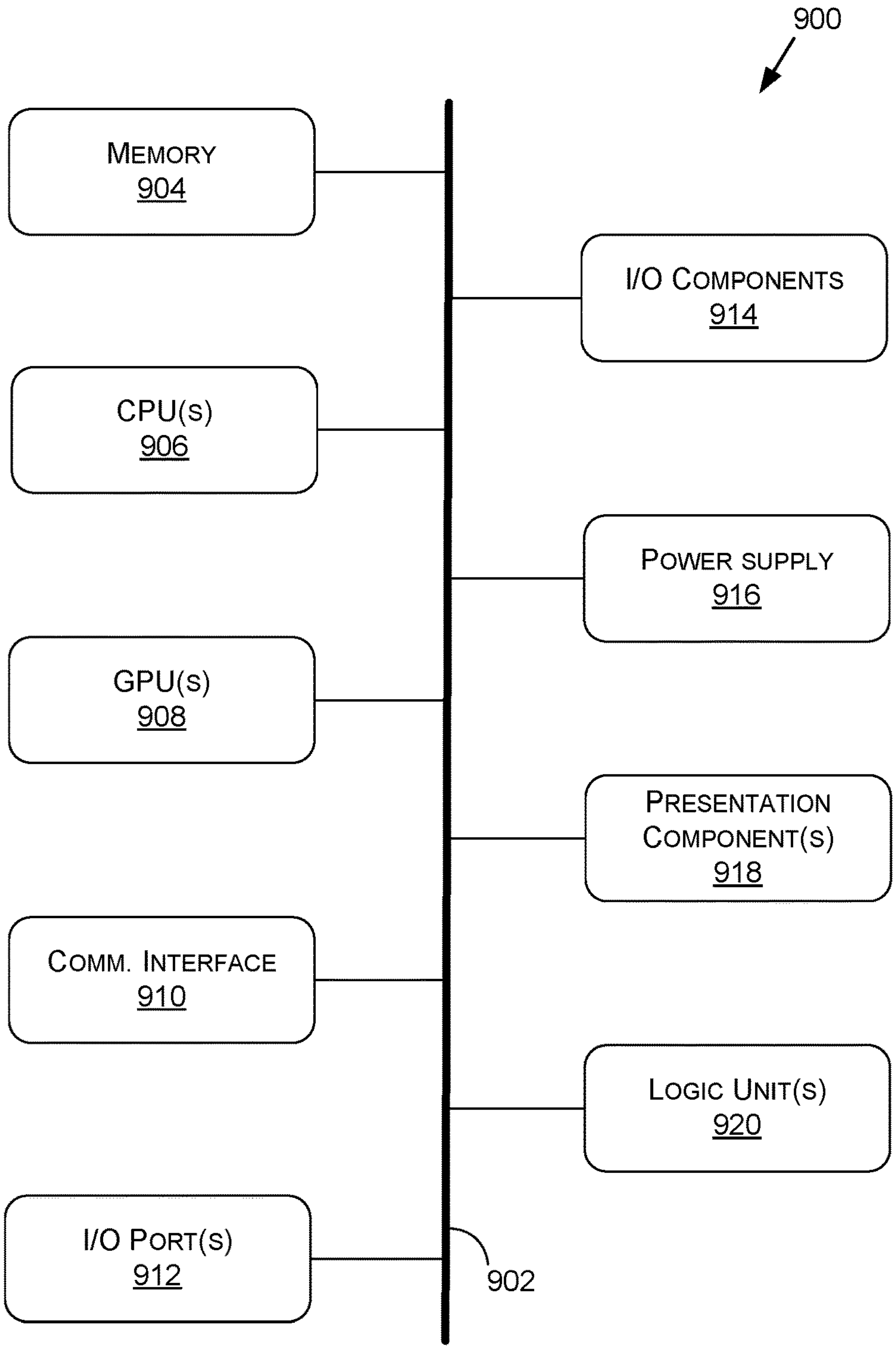
FIG. 9 is a block diagram of an example computing device suitable for use in implementing some embodiments of the present disclosure.

FIG. 9 is a block diagram of an example computing device(s) 900 suitable for use in implementing some embodiments of the present disclosure. Computing device 900 may include an interconnect system 902 that directly or indirectly couples the following devices: memory 904, one or more central processing units (CPUs) 906, one or more graphics processing units (GPUs) 908, a communication interface 910, input/output (I/O) ports 912, input/output components 914, a power supply 916, one or more presentation components 918 (e.g., display(s)), and one or more logic units 920. In at least one embodiment, the computing device(s) 900 may comprise one or more virtual machines (VMs), and/or any of the components thereof may comprise virtual components (e.g., virtual hardware components). For non-limiting examples, one or more of the GPUs 908 may comprise one or more vGPUs, one or more of the CPUs 906 may comprise one or more vCPUs, and/or one or more of the logic units 920 may comprise one or more virtual logic units. As such, a computing device(s) 900 may include discrete components (e.g., a full GPU dedicated to the computing device 900), virtual components (e.g., a portion of a GPU dedicated to the computing device 900), or a combination thereof.

Although the various blocks of FIG. 9 are shown as connected via the interconnect system 902 with lines, this is not intended to be limiting and is for clarity only. For example, in some embodiments, a presentation component 918, such as a display device, may be considered an I/O component 914 (e.g., if the display is a touch screen). As another example, the CPUs 906 and/or GPUs 908 may include memory (e.g., the memory 904 may be representative of a storage device in addition to the memory of the GPUs 908, the CPUs 906, and/or other components). In other words, the computing device of FIG. 9 is merely illustrative. Distinction is not made between such categories as "workstation," "server," "laptop," "desktop," "tablet," "client device," "mobile device," "hand-held device," "game console," "electronic control unit (ECU)," "virtual reality system," and/or other device or system types, as all are contemplated within the scope of the computing device of FIG. 9.

The interconnect system 902 may represent one or more links or busses, such as an address bus, a data bus, a control bus, or a combination thereof. The interconnect system 902 may include one or more bus or link types, such as an industry standard architecture (ISA) bus, an extended industry standard architecture (EISA) bus, a video electronics standards association (VESA) bus, a peripheral component interconnect (PCI) bus, a peripheral component interconnect express (PCIe) bus, and/or another type of bus or link. In some embodiments, there are direct connections between components. As an example, the CPU 906 may be directly connected to the memory 904. Further, the CPU 906 may be directly connected to the GPU 908. Where there is direct, or point-to-point connection between components, the interconnect system 902 may include a PCIe link to carry out the connection. In these examples, a PCI bus need not be included in the computing device 900.

The memory 904 may include any of a variety of computer-readable media. The computer-readable media may be any available media that may be accessed by the computing device 900. The computer-readable media may include both volatile and nonvolatile media, and removable and non-removable media. By way of example, and not limitation, the computer-readable media may comprise computer-storage media and communication media.

The computer-storage media may include both volatile and nonvolatile media and/or removable and non-removable media implemented in any method or technology for storage of information such as computer-readable instructions, data structures, program modules, and/or other data types. For example, the memory 904 may store computer-readable instructions (e.g., that represent a program(s) and/or a program element(s), such as an operating system. Computer-storage media may include, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which may be used to store the desired information and which may be accessed by computing device 900. As used herein, computer storage media does not comprise signals per se.

The computer storage media may embody computer-readable instructions, data structures, program modules, and/or other data types in a modulated data signal such as a carrier wave or other transport mechanism and includes any information delivery media. The term "modulated data signal" may refer to a signal that has one or more of its characteristics set or changed in such a manner as to encode information in the signal. By way of example, and not limitation, the computer storage media may include wired media such as a wired network or direct-wired connection, and wireless media such as acoustic, RF, infrared and other wireless media. Combinations of any of the above should also be included within the scope of computer-readable media.

The CPU(s) 906 may be configured to execute at least some of the computer-readable instructions to control one or more components of the computing device 900 to perform one or more of the methods and/or processes described herein. The CPU(s) 906 may each include one or more cores (e.g., one, two, four, eight, twenty-eight, seventy-two, etc.) that are capable of handling a multitude of software threads simultaneously. The CPU(s) 906 may include any type of processor, and may include different types of processors depending on the type of computing device 900 implemented (e.g., processors with fewer cores for mobile devices and processors with more cores for servers). For example, depending on the type of computing device 900, the processor may be an Advanced RISC Machines (ARM) processor implemented using Reduced Instruction Set Computing (RISC) or an x86 processor implemented using Complex Instruction Set Computing (CISC). The computing device 900 may include one or more CPUs 906 in addition to one or more microprocessors or supplementary co-processors, such as math co-processors. In some embodiments, the circadian rhythm-based ground truth correction system(s) and/or circadian rhythm-based drowsiness detection system(s) described herein may be implemented at least in part by code executed by the CPU(s) 906. In addition to or alternatively from the CPU(s) 906, the GPU(s) 908 may be configured to execute at least some of the computer-readable instructions to control one or more components of the computing device 900 to perform one or more of the methods and/or processes described herein. One or more of the GPU(s) 908 may be an integrated GPU (e.g., with one or more of the CPU(s) 906 and/or one or more of the GPU(s) 908 may be a discrete GPU. In embodiments, one or more of the GPU(s) 908 may be a coprocessor of one or more of the CPU(s) 906. The GPU(s) 908 may be used by the computing device 900 to render graphics (e.g., 3D graphics) or perform general purpose computations. For example, the GPU(s) 908 may be used for General-Purpose computing on GPUs (GPGPU). The GPU(s) 908 may include hundreds or thousands of cores that are capable of handling hundreds or thousands of software threads simultaneously. The GPU(s) 908 may generate pixel data for output images in response to rendering commands (e.g., rendering commands from the CPU(s) 906 received via a host interface). The GPU(s) 908 may include graphics memory, such as display memory, for storing pixel data or any other suitable data, such as GPGPU data. The display memory may be included as part of the memory 904. The GPU(s) 908 may include two or more GPUs operating in parallel (e.g., via a link). The link may directly connect the GPUs (e.g., using NVLINK) or may connect the GPUs through a switch (e.g., using NVSwitch). When combined together, each GPU 908 may generate pixel data or GPGPU data for different portions of an output or for different outputs (e.g., a first GPU for a first image and a second GPU for a second image). Each GPU may include its own memory, or may share memory with other GPUs. In some embodiments, drowsiness machine learning model 170 and/or drowsiness machine learning model 312 may be implemented, at least in part, by code executed by GPU(s) 908.

In addition to or alternatively from the CPU(s) 906 and/or the GPU(s) 908, the logic unit(s) 920 may be configured to execute at least some of the computer-readable instructions to control one or more components of the computing device 900 to perform one or more of the methods and/or processes described herein. In embodiments, the CPU(s) 906, the GPU(s) 908, and/or the logic unit(s) 920 may discretely or jointly perform any combination of the methods, processes and/or portions thereof. One or more of the logic units 920 may be part of and/or integrated in one or more of the CPU(s) 906 and/or the GPU(s) 908 and/or one or more of the logic units 920 may be discrete components or otherwise external to the CPU(s) 906 and/or the GPU(s) 908. In embodiments, one or more of the logic units 920 may be a coprocessor of one or more of the CPU(s) 906 and/or one or more of the GPU(s) 908.

Examples of the logic unit(s) 920 include one or more processing cores and/or components thereof, such as Data Processing Units (DPUs), Tensor Cores (TCs), Tensor Processing Units (TPUs), Pixel Visual Cores (PVCs), Vision Processing Units (VPUs), Graphics Processing Clusters (GPCs), Texture Processing Clusters (TPCs), Streaming Multiprocessors (SMs), Tree Traversal Units (TTUs), Artificial Intelligence Accelerators (AIAs), Deep Learning Accelerators (DLAs), Arithmetic-Logic Units (ALUs), Application-Specific Integrated Circuits (ASICs), Floating Point Units (FPUs), input/output (I/O) elements, peripheral component interconnect (PCI) or peripheral component interconnect express (PCIe) elements, and/or the like.

The communication interface 910 may include one or more receivers, transmitters, and/or transceivers that enable the computing device 900 to communicate with other computing devices via an electronic communication network, included wired and/or wireless communications. The communication interface 910 may include components and functionality to enable communication over any of a number of different networks, such as wireless networks (e.g., Wi-Fi, Z-Wave, Bluetooth, Bluetooth LE, ZigBee, etc.), wired networks (e.g., communicating over Ethernet or InfiniBand), low-power wide-area networks (e.g., LoRaWAN, SigFox, etc.), and/or the Internet. In one or more embodiments, logic unit(s) 920 and/or communication interface 910 may include one or more data processing units (DPUs) to transmit data received over a network and/or through interconnect system 902 directly to (e.g., a memory of) one or more GPU(s) 908.

The I/O ports 912 may enable the computing device 900 to be logically coupled to other devices including the I/O components 914, the presentation component(s) 918, and/or other components, some of which may be built in to (e.g., integrated in) the computing device 900. Illustrative I/O components 914 include a microphone, mouse, keyboard, joystick, game pad, game controller, satellite dish, scanner, printer, wireless device, etc. The I/O components 914 may provide a natural user interface (NUI) that processes air gestures, voice, or other physiological inputs generated by a user. In some instances, inputs may be transmitted to an appropriate network element for further processing. An NUI may implement any combination of speech recognition, stylus recognition, facial recognition, biometric recognition, gesture recognition both on screen and adjacent to the screen, air gestures, head and eye tracking, and touch recognition (as described in more detail below) associated with a display of the computing device 900. The computing device 900 may be include depth cameras, such as stereoscopic camera systems, infrared camera systems, RGB camera systems, touchscreen technology, and combinations of these, for gesture detection and recognition. Additionally, the computing device 900 may include accelerometers or gyroscopes (e.g., as part of an inertia measurement unit (IMU)) that enable detection of motion. In some examples, the output of the accelerometers or gyroscopes may be used by the computing device 900 to render immersive augmented reality or virtual reality.

The power supply 916 may include a hard-wired power supply, a battery power supply, or a combination thereof. The power supply 916 may provide power to the computing device 900 to enable the components of the computing device 900 to operate.

The presentation component(s) 918 may include a display (e.g., a monitor, a touch screen, a television screen, a heads-up-display (HUD), other display types, or a combination thereof), speakers, and/or other presentation components. The presentation component(s) 918 may receive data from other components (e.g., the GPU(s) 908, the CPU(s) 906, DPUs, etc.), and output the data (e.g., as an image, video, sound, etc.).

Example Data Center

Figure 10:
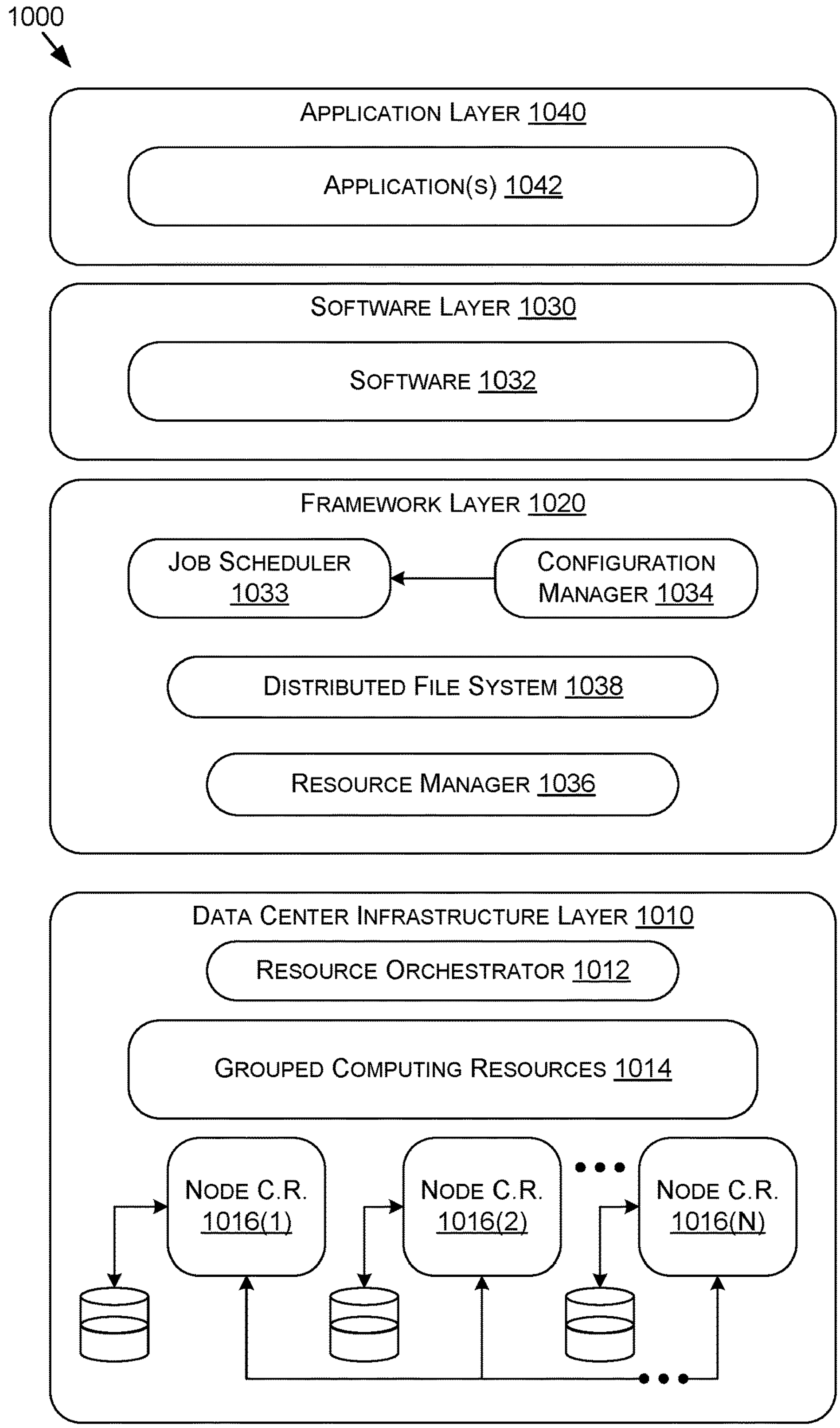
FIG. 10 is a block diagram of an example data center suitable for use in implementing some embodiments of the present disclosure.

FIG. 10 illustrates an example data center 1000 that may be used in at least one embodiments of the present disclosure. The data center 1000 may include a data center infrastructure layer 1010, a framework layer 1020, a software layer 1030, and/or an application layer 1040.

As shown in FIG. 10, the data center infrastructure layer 1010 may include a resource orchestrator 1012, grouped computing resources 1014, and node computing resources ("node C.R.s") 1016(1)-1016(N), where "N" represents any whole, positive integer. In at least one embodiment, node C.R.s 1016(1)-1016(N) may include, but are not limited to, any number of central processing units (CPUs) or other processors (including DPUs, accelerators, field programmable gate arrays (FPGAs), graphics processors or graphics processing units (GPUs), etc.), memory devices (e.g., dynamic read-only memory), storage devices (e.g., solid state or disk drives), network input/output (NW I/O) devices, network switches, virtual machines (VMs), power modules, and/or cooling modules, etc. In some embodiments, one or more node C.R.s from among node C.R.s 1016(1)-1016(N) may correspond to a server having one or more of the above-mentioned computing resources. In addition, in some embodiments, the node C.R.s 1016(1)-10161 (N) may include one or more virtual components, such as vGPUs, vCPUs, and/or the like, and/or one or more of the node C.R.s 1016(1)-1016(N) may correspond to a virtual machine (VM). In some embodiments, one or more aspects of the circadian rhythm-based ground truth correction system(s) and/or circadian rhythm-based drowsiness detection system(s) may be implemented by one or more of the node C.R.s 1016(1)-1016(N).

In at least one embodiment, grouped computing resources 1014 may include separate groupings of node C.R.s 1016 housed within one or more racks (not shown), or many racks housed in data centers at various geographical locations (also not shown). Separate groupings of node C.R.s 1016 within grouped computing resources 1014 may include grouped compute, network, memory or storage resources that may be configured or allocated to support one or more workloads. In at least one embodiment, several node C.R.s 1016 including CPUs, GPUs, DPUs, and/or other processors may be grouped within one or more racks to provide compute resources to support one or more workloads. The one or more racks may also include any number of power modules, cooling modules, and/or network switches, in any combination.

The resource orchestrator 1012 may configure or otherwise control one or more node C.R.s 1016(1)-1016(N) and/or grouped computing resources 1014. In at least one embodiment, resource orchestrator 1012 may include a software design infrastructure (SDI) management entity for the data center 1000. The resource orchestrator 1012 may include hardware, software, or some combination thereof.

In at least one embodiment, as shown in FIG. 10, framework layer 1020 may include a job scheduler 1033, a configuration manager 1034, a resource manager 1036, and/or a distributed file system 1038. The framework layer 1020 may include a framework to support software 1032 of software layer 1030 and/or one or more application(s) 1042 of application layer 1040. The software 1032 or application(s) 1042 may respectively include web-based service software or applications, such as those provided by Amazon Web Services, Google Cloud and Microsoft Azure. The framework layer 1020 may be, but is not limited to, a type of free and open-source software web application framework such as Apache Spark™ (hereinafter "Spark") that may utilize distributed file system 1038 for large-scale data processing (e.g., "big data"). In at least one embodiment, job scheduler 1033 may include a Spark driver to facilitate scheduling of workloads supported by various layers of data center 1000. The configuration manager 1034 may be capable of configuring different layers such as software layer 1030 and framework layer 1020 including Spark and distributed file system 1038 for supporting large-scale data processing. The resource manager 1036 may be capable of managing clustered or grouped computing resources mapped to or allocated for support of distributed file system 1038 and job scheduler 1033. In at least one embodiment, clustered or grouped computing resources may include grouped computing resource 1014 at data center infrastructure layer 1010. The resource manager 1036 may coordinate with resource orchestrator 1012 to manage these mapped or allocated computing resources.

In at least one embodiment, software 1032 included in software layer 1030 may include software used by at least portions of node C.R.s 1016(1)-1016(N), grouped computing resources 1014, and/or distributed file system 1038 of framework layer 1020. One or more types of software may include, but are not limited to, Internet web page search software, e-mail virus scan software, database software, and streaming video content software.

In at least one embodiment, application(s) 1042 included in application layer 1040 may include one or more types of applications used by at least portions of node C.R.s 1016 (1)-1016 (N), grouped computing resources 1014, and/or distributed file system 1038 of framework layer 1020. One or more types of applications may include, but are not limited to, any number of a genomics application, a cognitive compute, and a machine learning application, including training or inferencing software, machine learning framework software (e.g., PyTorch, TensorFlow, Caffe, etc.), and/or other machine learning applications used in conjunction with one or more embodiments.

In at least one embodiment, any of configuration manager 1034, resource manager 1036, and resource orchestrator 1012 may implement any number and type of self-modifying actions based on any amount and type of data acquired in any technically feasible fashion. Self-modifying actions may relieve a data center operator of data center 1000 from making possibly bad configuration decisions and possibly avoiding underutilized and/or poor performing portions of a data center.

The data center 1000 may include tools, services, software or other resources to train one or more machine learning models or predict or infer information using one or more machine learning models according to one or more embodiments described herein. For example, a machine learning model(s) may be trained by calculating weight parameters according to a neural network architecture using software and/or computing resources described above with respect to the data center 1000. In at least one embodiment, trained or deployed machine learning models corresponding to one or more neural networks may be used to infer or predict information using resources described above with respect to the data center 1000 by using weight parameters calculated through one or more training techniques, such as but not limited to those described herein.

In at least one embodiment, the data center 1000 may use CPUs, application-specific integrated circuits (ASICs), GPUs, FPGAs, and/or other hardware (or virtual compute resources corresponding thereto) to perform training and/or inferencing using above-described resources. Moreover, one or more software and/or hardware resources described above may be configured as a service to allow users to train or performing inferencing of information, such as image recognition, speech recognition, or other artificial intelligence services.

Example Network Environments

Network environments suitable for use in implementing embodiments of the disclosure may include one or more client devices, servers, network attached storage (NAS), other backend devices, and/or other device types. The client devices, servers, and/or other device types (e.g., each device) may be implemented on one or more instances of the computing device(s) 900 of FIG. 9—e.g., each device may include similar components, features, and/or functionality of the computing device(s) 900. In addition, where backend devices (e.g., servers, NAS, etc.) are implemented, the backend devices may be included as part of a data center 1000, an example of which is described in more detail herein with respect to FIG. 10.

Components of a network environment may communicate with each other via a network(s), which may be wired, wireless, or both. The network may include multiple networks, or a network of networks. By way of example, the network may include one or more Wide Area Networks (WANs), one or more Local Area Networks (LANs), one or more public networks such as the Internet and/or a public switched telephone network (PSTN), and/or one or more private networks. Where the network includes a wireless telecommunications network, components such as a base station, a communications tower, or even access points (as well as other components) may provide wireless connectivity.

Compatible network environments may include one or more peer-to-peer network environments—in which case a server may not be included in a network environment—and one or more client-server network environments—in which case one or more servers may be included in a network environment. In peer-to-peer network environments, functionality described herein with respect to a server(s) may be implemented on any number of client devices.

In at least one embodiment, a network environment may include one or more cloud-based network environments, a distributed computing environment, a combination thereof, etc. A cloud-based network environment may include a framework layer, a job scheduler, a resource manager, and a distributed file system implemented on one or more of servers, which may include one or more core network servers and/or edge servers. A framework layer may include a framework to support software of a software layer and/or one or more application(s) of an application layer. The software or application(s) may respectively include web-based service software or applications. In embodiments, one or more of the client devices may use the web-based service software or applications (e.g., by accessing the service software and/or applications via one or more application programming interfaces (APIs)). The framework layer may be, but is not limited to, a type of free and open-source software web application framework such as that may use a distributed file system for large-scale data processing (e.g., "big data").

A cloud-based network environment may provide cloud computing and/or cloud storage that carries out any combination of computing and/or data storage functions described herein (or one or more portions thereof). Any of these various functions may be distributed over multiple locations from central or core servers (e.g., of one or more data centers that may be distributed across a state, a region, a country, the globe, etc.). If a connection to a user (e.g., a client device) is relatively close to an edge server(s), a core server(s) may designate at least a portion of the functionality to the edge server(s). A cloud-based network environment may be private (e.g., limited to a single organization), may be public (e.g., available to many organizations), and/or a combination thereof (e.g., a hybrid cloud environment).

The client device(s) may include at least some of the components, features, and functionality of the example computing device(s) 900 described herein with respect to FIG. 9. By way of example and not limitation, a client device may be embodied as a Personal Computer (PC), a laptop computer, a mobile device, a smartphone, a tablet computer, a smart watch, a wearable computer, a Personal Digital Assistant (PDA), an MP3 player, a virtual reality headset, a Global Positioning System (GPS) or device, a video player, a video camera, a surveillance device or system, a vehicle, a boat, a flying vessel, a virtual machine, a drone, a robot, a handheld communications device, a hospital device, a gaming device or system, an entertainment system, a vehicle computer system, an embedded system controller, a remote control, an appliance, a consumer electronic device, a workstation, an edge device, any combination of these delineated devices, or any other suitable device.

The disclosure may be described in the general context of computer code or machine-useable instructions, including computer-executable instructions such as program modules, being executed by a computer or other machine, such as a personal data assistant or other handheld device. Generally, program modules including routines, programs, objects, components, data structures, etc., refer to code that perform particular tasks or implement particular abstract data types. The disclosure may be practiced in a variety of system configurations, including hand-held devices, consumer electronics, general-purpose computers, more specialty computing devices, etc. The disclosure may also be practiced in distributed computing environments where tasks are performed by remote-processing devices that are linked through a communications network.

As used herein, a recitation of "and/or" with respect to two or more elements should be interpreted to mean only one element, or a combination of elements. For example, "element A, element B, and/or element C" may include only element A, only element B, only element C, element A and element B, element A and element C, element B and element C, or elements A, B, and C. In addition, "at least one of element A or element B" may include at least one of element A, at least one of element B, or at least one of element A and at least one of element B. Further, "at least one of element A and element B" may include at least one of element A, at least one of element B, or at least one of element A and at least one of element B.

The subject matter of the present disclosure is described with specificity herein to meet statutory requirements. However, the description itself is not intended to limit the scope of this disclosure. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

What is claimed is:

1. One or more processors comprising one or more processing units to:

receive a first ground truth image sequence representing visual characteristics of a test subject in the first ground truth image sequence during a testing period, the first ground truth image sequence comprising one or more drowsiness labels indicating a drowsiness of the test subject;

correlate a position on a circadian rhythm process to a time of the testing period;

apply one or more drowsiness corrections to the one or more drowsiness labels based at least on an alertness value corresponding to the position on the circadian rhythm process, to generate a second ground truth image sequence; and train a machine learning model to infer a drowsiness level based on the second ground truth image sequence.

2. The one or more processors of claim 1, wherein the one or more processing units are further to:

determine the alertness value corresponding to the position on the circadian rhythm process based at least on a time of day and sensor data representing sleep information measured from the test subject.

3. The one or more processors of claim 1, wherein the one or more processing units are further to:

determine the alertness value corresponding to the position on the circadian rhythm process based at least on a time of day and sleep information based at least on responses to questions to the test subject.

4. The one or more processors of claim 1, wherein the one or more processing units are further to:

compute the one or more drowsiness corrections based at least on the alertness value corresponding to the position on the circadian rhythm process and time-on-task data associated with a task performed by the test subject during the testing period.

5. The one or more processors of claim 1, wherein the one or more processing units are further to:

compute the one or more drowsiness corrections based at least on the alertness value corresponding to the position on the circadian rhythm process and one or more alertness test measurements captured from the test subject during the testing period.

6. The one or more processors of claim 5, wherein the one or more alertness test measurements comprise at least one of an electroencephalogram (EEG) test and a mean reaction time (MRT) measurement.

7. The one or more processors of claim 1, wherein the first ground truth image sequence captures visual characteristics of the test subject performing one or more psychomotor vigilance tests (PVTs) over a course of the testing period.

8. The one or more processors of claim 1, wherein one or more drowsiness labels of the second ground truth image sequence comprise a score based at least on a Karolinska Sleepiness Scale (KSS).

9. The one or more processors of claim 1, wherein visual characteristics of the test subject in the first ground truth image sequence comprise at least one of an eye blink rate, an eye blink velocity, an eye blink amplitude, a time of eye closure, a head pose, an eye gaze direction, and a pattern of yawning behavior.

10. The one or more processors of claim 1, wherein the circadian rhythm process corresponds to a circadian rhythm process C curve.

11. The one or more processors of claim 1, wherein the one or more processors are comprised in at least one of:

a control system for an autonomous or semi-autonomous machine;
a perception system for an autonomous or semi-autonomous machine;
a system for performing simulation operations;
a system for performing digital twin operations;
a system for performing light transport simulation;
a system for performing collaborative content creation for three-dimensional assets;
a system for performing deep learning operations;
a system for performing remote operations;
a system for performing real-time streaming;
a system for generating or presenting one or more of augmented reality content, virtual reality content, or mixed reality content;
a system implemented using an edge device;
a system implemented using a robot;
a system for performing conversational AI operations;
a system implementing one or more language models;
a system implementing one or more large language models (LLMs);
a system for generating synthetic data;
a system for generating synthetic data using AI;
a system incorporating one or more virtual machines (VMs);
a system implemented at least partially in a data center; or
a system implemented at least partially using cloud computing resources.

12. A system comprising:

one or more processing units to:

determine a drowsiness score estimate for a test subject during a testing period based at least on correlating a circadian rhythm process to the test subject at a time of the testing period;

apply one or more drowsiness corrections based at least on the drowsiness score estimate to a first ground truth image sequence representing visual characteristics of the test subject during the testing period to generate a second ground truth image sequence, the one or more drowsiness corrections correcting one or more drowsiness labels of the first ground truth image sequence; and train a machine learning model using the second ground truth image sequence to infer a drowsiness level.

13. The system of claim 12, wherein the one or more processing units are further to:

determine the drowsiness score estimate based at least on a circadian rhythm process C curve.

14. The system of claim 12, wherein visual characteristics of the test subject in the first ground truth image sequence comprise at least one of an eye blink rate, an eye blink velocity, an eye blink amplitude, a time of eye closure, a head pose, an eye gaze direction, and a pattern of yawning behavior.

15. The system of claim 12, wherein the one or more processing units are further to:

determine the drowsiness score estimate based at least on an alertness value corresponding to a position on the circadian rhythm process, the position determined based at least on a time of day and sensor data representing sleep information measured from the test subject.

16. The system of claim 12, wherein the one or more processing units are further to:

determine the drowsiness score estimate based at least on an alertness value corresponding to a position on the circadian rhythm process, the position determined based at least on a time of day and sleep information based at least on responses to questions to the test subject.

17. The system of claim 12, wherein the one or more processing units are further to:

compute the one or more drowsiness corrections based at least on an alertness value corresponding to a position on the circadian rhythm process and time-on-task data associated with a task performed by the test subject during the testing period.

18. The system of claim 12, wherein the one or more processing units are further to:

compute the one or more drowsiness corrections based at least on an alertness value corresponding to a position on the circadian rhythm process and one or more alertness test measurements captured from the test subject during the testing period.

19. The system of claim 12, wherein the one or more processing units are comprised in at least one of:

a control system for an autonomous or semi-autonomous machine;
a perception system for an autonomous or semi-autonomous machine;
a system for performing simulation operations;
a system for performing digital twin operations;
a system for performing light transport simulation;

a system for performing collaborative content creation for three-dimensional assets;
a system for performing deep learning operations;
a system for performing remote operations;
a system for performing real-time streaming;
a system for generating or presenting one or more of augmented reality content, virtual reality content, or mixed reality content;
a system implemented using an edge device;
a system implemented using a robot;
a system for performing conversational AI operations;
a system implementing one or more language models;
a system implementing one or more large language models (LLMs);
a system for generating synthetic data;
a system for generating synthetic data using AI;
a system incorporating one or more virtual machines (VMs);
a system implemented at least partially in a data center; or
a system implemented at least partially using cloud computing resources.

20. A method comprising:
generating a second ground truth image sequence from a first ground truth image sequence by applying one or more drowsiness corrections to one or more labels of the first ground truth image sequence, the one or more drowsiness corrections determined using a drowsiness score estimate for a test subject during a testing period associated with the first ground truth image sequence, the drowsiness score estimate based at least on correlating a circadian rhythm process to the test subject at a time of the testing period.

* * * * *